(12) United States Patent
Hebert

(10) Patent No.: US 10,029,072 B2
(45) Date of Patent: Jul. 24, 2018

(54) COAXIAL BI-DIRECTIONAL CATHETER

(71) Applicant: Curvo Medical, Inc., San Francisco, CA (US)

(72) Inventor: Stephen J. Hebert, San Francisco, CA (US)

(73) Assignee: Curvo Medical, Inc., San Francisco, CA (US)

( * ) Notice: Subject to any disclaimer, the term of this patent is extended or adjusted under 35 U.S.C. 154(b) by 67 days.

(21) Appl. No.: 15/368,593

(22) Filed: Dec. 3, 2016

(65) Prior Publication Data

US 2017/0189646 A1    Jul. 6, 2017

Related U.S. Application Data

(60) Continuation of application No. 15/055,553, filed on Feb. 27, 2016, which is a continuation of application (Continued)

(51) Int. Cl.
*A61M 25/01*    (2006.01)

(52) U.S. Cl.
CPC .... *A61M 25/0138* (2013.01); *A61M 25/0144* (2013.01); *A61M 25/0147* (2013.01)

(58) Field of Classification Search
CPC ............ A61M 25/005; A61M 25/0138; A61M 25/0144; A61M 25/0147; A61M 25/0068; A61M 2525/0161

See application file for complete search history.

(56) References Cited

U.S. PATENT DOCUMENTS 4,245,624 A * 1/1981 Komiya ............. A61B 1/00098
                                                   600/106
4,548,206 A * 10/1985 Osborne ......... A61M 25/09025
                                                   600/585

(Continued)

FOREIGN PATENT DOCUMENTS

CN    101433469    5/2009
EP    1346747     9/2003

(Continued)

OTHER PUBLICATIONS

PCT/US2013/069435 International Search Report (dated Nov. 11, 2013).

(Continued)

*Primary Examiner* — Quynh-Nhu H Vu
(74) *Attorney, Agent, or Firm* — Neil D. Gershon

(57) ABSTRACT

A deflectable catheter including an outer member having a proximal portion and a distal portion, an elongated column member extending distally from the outer member and an inner member positioned coaxial with the outer member and attached to the column member. The inner member extends distally of the outer member and has a distal tip portion. A reinforcement member is positioned over the column member to restrict axial movement of the column member such that when one of the inner member or outer member is moved with respect to the other, axial compression of the column member is restricted by the reinforcement member causing the distal tip portion of the inner member to deflect laterally.

19 Claims, 13 Drawing Sheets

Related U.S. Application Data

No. 14/846,671, filed on Sep. 4, 2015, which is a division of application No. 14/064,170, filed on Oct. 27, 2013, now Pat. No. 9,233,225.

(60) Provisional application No. 61/724,921, filed on Nov. 10, 2012.

(56) References Cited

U.S. PATENT DOCUMENTS

| | | | |
|---|---|---|---|
| 4,723,936 A | 2/1988 | Buchbinder et al. | |
| 4,739,786 A | 4/1988 | Parkinson | |
| 4,927,413 A | 5/1990 | Hess | |
| 4,940,062 A * | 7/1990 | Hampton | A61M 25/09033 600/434 |
| 4,960,134 A | 10/1990 | Webster, Jr. | |
| 5,152,744 A | 10/1992 | Krause | |
| 5,169,568 A | 12/1992 | Ainger, III | |
| 5,199,417 A | 4/1993 | Mueller et al. | |
| 5,325,845 A | 7/1994 | Adair | |
| 5,381,782 A * | 1/1995 | DeLaRama | A61B 1/0056 138/118 |
| 5,383,923 A | 1/1995 | Webster, Jr. | |
| 5,396,880 A | 3/1995 | Kagan | |
| 5,431,168 A | 7/1995 | Webster, Jr. | |
| 5,441,483 A | 8/1995 | Avitall | |
| 5,470,330 A | 11/1995 | Goldenberg et al. | |
| 5,480,382 A | 1/1996 | Hammerslag et al. | |
| 5,484,433 A | 1/1996 | Taylor et al. | |
| 5,562,619 A | 10/1996 | Mirarchi et al. | |
| 5,611,777 A | 3/1997 | Bowden et al. | |
| 5,632,734 A | 5/1997 | Galel et al. | |
| 5,715,832 A | 2/1998 | Koblish et al. | |
| 5,820,592 A | 10/1998 | Hammerslag | |
| 5,853,368 A | 12/1998 | Solomon | |
| 5,921,978 A | 7/1999 | Thompson et al. | |
| 6,083,222 A | 7/2000 | Klein et al. | |
| 6,092,526 A | 7/2000 | LaFointaine et al. | |
| 6,096,022 A | 8/2000 | Laymon et al. | |
| 6,123,699 A | 9/2000 | Webster, Jr. | |
| 6,126,649 A * | 10/2000 | VanTassel | A61M 25/0138 604/528 |
| 6,200,315 B1 | 3/2001 | Gaiser | |
| 6,493,575 B1 | 12/2002 | Kesten et al. | |
| 6,500,167 B1 | 12/2002 | Webster, Jr. | |
| 6,527,769 B2 | 3/2003 | Langberg et al. | |
| 6,554,794 B1 | 4/2003 | Mueller et al. | |
| 6,572,593 B1 | 6/2003 | Daum | |
| 6,640,120 B1 | 10/2003 | Swanson et al. | |
| 6,671,550 B2 | 12/2003 | Iaizzo et al. | |
| 6,726,700 B1 | 4/2004 | Levine | |
| 6,733,500 B2 | 5/2004 | Kelley et al. | |
| 6,743,227 B2 | 6/2004 | Seraj et al. | |
| 6,778,846 B1 | 8/2004 | Martinez et al. | |
| 6,836,687 B2 | 12/2004 | Kelley et al. | |
| 6,893,436 B2 | 5/2005 | Woodard et al. | |
| 6,926,711 B2 | 8/2005 | Lentz et al. | |
| 6,936,047 B2 | 8/2005 | Nasab et al. | |
| 6,951,554 B2 | 10/2005 | Johansen et al. | |
| 7,027,851 B2 | 4/2006 | Meija | |
| 7,039,450 B2 | 5/2006 | Duarte | |
| 7,089,063 B2 | 8/2006 | Lesh et al. | |
| 7,099,717 B2 | 8/2006 | Woodard et al. | |
| 7,252,664 B2 | 8/2007 | Nasab et al. | |
| 7,481,778 B2 | 1/2009 | Cedro et al. | |
| 7,497,844 B2 | 3/2009 | Spear et al. | |
| 7,507,205 B2 | 3/2009 | Borovsky et al. | |
| 7,565,208 B2 | 7/2009 | Harris et al. | |
| 7,569,626 B2 | 8/2009 | Truckai et al. | |
| 7,591,813 B2 | 9/2009 | Levine et al. | |
| 7,615,032 B2 | 11/2009 | Whittaker et al. | |
| 7,615,044 B2 | 11/2009 | Scheibe et al. | |
| 7,641,480 B1 | 1/2010 | Hossack et al. | |
| 7,648,517 B2 | 1/2010 | Makaower et al. | |
| 7,674,253 B2 | 3/2010 | Fisher et al. | |
| 7,694,683 B2 | 4/2010 | Callister et al. | |
| 7,699,829 B2 | 4/2010 | Harris et al. | |
| 7,717,853 B2 | 5/2010 | Nita | |
| 7,731,681 B2 | 6/2010 | Schaer et al. | |
| 7,736,346 B2 | 6/2010 | Miller et al. | |
| 7,766,868 B2 | 8/2010 | Goode et al. | |
| 7,766,961 B2 | 8/2010 | Patel et al. | |
| 7,771,388 B2 | 8/2010 | Olsen et al. | |
| 7,794,454 B2 | 9/2010 | Abboud et al. | |
| 7,815,577 B2 | 10/2010 | Krishnan | |
| 7,818,040 B2 | 10/2010 | Spear et al. | |
| 7,824,517 B2 | 11/2010 | Kampa et al. | |
| 7,867,194 B2 | 1/2011 | Fiering et al. | |
| 7,881,769 B2 | 2/2011 | Sobe | |
| 7,909,797 B2 | 3/2011 | Kennedy, II et al. | |
| 7,914,503 B2 | 3/2011 | Goodson, IV et al. | |
| 7,918,819 B2 | 4/2011 | Karmarkar et al. | |
| 7,922,650 B2 | 4/2011 | McWeeney et al. | |
| 7,922,654 B2 | 4/2011 | Boutillette et al. | |
| 7,942,850 B2 | 5/2011 | Levit et al. | |
| 7,967,830 B2 | 6/2011 | Ayala et al. | |
| 7,976,528 B2 | 7/2011 | Nash et al. | |
| 7,988,646 B2 | 8/2011 | Tabar | |
| 7,998,112 B2 | 8/2011 | Chow | |
| 8,075,498 B2 | 12/2011 | Leo et al. | |
| 8,118,803 B1 | 2/2012 | Chow et al. | |
| 8,147,481 B2 | 4/2012 | Whittaker et al. | |
| 8,147,502 B2 * | 4/2012 | Albrecht | A61B 17/0218 606/119 |
| 8,152,799 B2 | 4/2012 | Ormsby et al. | |
| 8,172,828 B2 | 5/2012 | Chang et al. | |
| 8,172,829 B2 | 5/2012 | Farnholtz | |
| 8,195,297 B2 | 6/2012 | Penner | |
| 8,206,320 B2 | 6/2012 | Deal et al. | |
| 8,211,011 B2 | 7/2012 | Whayne et al. | |
| 8,211,087 B2 | 7/2012 | Carter et al. | |
| 8,211,171 B2 | 7/2012 | Kim et al. | |
| 8,213,075 B2 | 7/2012 | Chui et al. | |
| 8,214,018 B2 | 7/2012 | Markowitz et al. | |
| 8,216,224 B2 | 7/2012 | Morris et al. | |
| 8,216,256 B2 | 7/2012 | Raschdorf, Jr. et al. | |
| 8,216,277 B2 | 7/2012 | Zucherman et al. | |
| 8,216,281 B2 | 7/2012 | Winslow et al. | |
| 8,220,466 B2 | 7/2012 | Frazier et al. | |
| 8,220,487 B2 | 7/2012 | Unger et al. | |
| 8,220,494 B2 | 7/2012 | Struder et al. | |
| 8,221,396 B2 | 7/2012 | Dehnad et al. | |
| 8,221,402 B2 | 7/2012 | Francischelli et al. | |
| 8,221,463 B2 | 7/2012 | Zucherman et al. | |
| 8,222,023 B2 | 7/2012 | Battrell et al. | |
| 8,224,422 B2 | 7/2012 | Mottola et al. | |
| 8,224,438 B2 | 7/2012 | Levin | |
| 8,226,246 B2 | 7/2012 | Shirai et al. | |
| 8,228,593 B2 | 7/2012 | Shirai et al. | |
| 8,228,594 B2 | 7/2012 | Shirai et al. | |
| 8,231,613 B2 | 7/2012 | Baxter et al. | |
| 8,231,639 B2 | 7/2012 | Bolduc et al. | |
| 8,234,824 B2 | 8/2012 | Botkin et al. | |
| 8,235,047 B2 | 8/2012 | Swann et al. | |
| 8,235,468 B2 | 8/2012 | Fookes et al. | |
| 8,235,997 B2 | 8/2012 | Hoffman et al. | |
| 8,236,033 B2 | 8/2012 | Paul | |
| 8,238,013 B2 | 8/2012 | Ichikawa et al. | |
| 8,238,019 B2 | 8/2012 | Endo et al. | |
| 8,239,001 B2 | 8/2012 | Verard et al. | |
| 8,241,494 B2 | 8/2012 | Assion | |
| 8,247,178 B2 | 8/2012 | McBride et al. | |
| 8,256,585 B2 | 9/2012 | Halford et al. | |
| 8,256,628 B2 | 9/2012 | Stafford et al. | |
| 8,257,369 B2 | 9/2012 | Gellman et al. | |
| 8,257,397 B2 | 9/2012 | Winslow et al. | |
| 8,260,399 B2 | 9/2012 | Karmarker et al. | |
| 8,267,979 B2 | 9/2012 | Flynn et al. | |
| 8,268,446 B2 | 9/2012 | Desimone et al. | |
| 8,270,061 B2 | 9/2012 | Endo et al. | |
| 8,271,069 B2 | 9/2012 | Jascob et al. | |
| 8,273,073 B2 | 9/2012 | Levine et al. | |
| 8,273,086 B2 | 9/2012 | Serhan et al. | |
| 8,273,107 B2 | 9/2012 | Zucherman et al. | |

(56) References Cited

U.S. PATENT DOCUMENTS

| | | |
|---|---|---|
| 8,273,241 B2 | 9/2012 | Feldman et al. |
| 8,273,574 B2 | 9/2012 | Quake et al. |
| 8,323,241 B2 | 12/2012 | Salahieh et al. |
| 8,388,572 B2 | 3/2013 | Olsen et al. |
| 8,920,369 B2 | 12/2014 | Salahieh et al. |
| 9,174,022 B2 | 11/2015 | Uihlein |
| 2002/0068924 A1 | 6/2002 | Sinofsky |
| 2002/0072712 A1 | 6/2002 | Nool et al. |
| 2002/0161330 A1 | 10/2002 | Nguyen |
| 2003/0114844 A1 | 6/2003 | Ormsby et al. |
| 2004/0097804 A1 | 5/2004 | Sobe |
| 2004/0116851 A1 | 6/2004 | Johansen et al. |
| 2004/0176741 A1 | 9/2004 | Famholtz |
| 2004/0225256 A1 | 11/2004 | Ponzi et al. |
| 2005/0010237 A1 | 1/2005 | Niazi |
| 2005/0020914 A1 | 1/2005 | Amundson et al. |
| 2005/0054976 A1 | 3/2005 | Goode et al. |
| 2005/0070794 A1 | 3/2005 | Deal et al. |
| 2005/0070821 A1 | 3/2005 | Deal et al. |
| 2005/0143770 A1 | 6/2005 | Carter et al. |
| 2005/0187519 A1 | 8/2005 | Harris et al. |
| 2005/0222557 A1 | 10/2005 | Baxter et al. |
| 2005/0222558 A1 | 10/2005 | Baxter et al. |
| 2005/0234436 A1 | 10/2005 | Baxter et al. |
| 2005/0234437 A1 | 10/2005 | Baxter et al. |
| 2005/0273020 A1 | 12/2005 | Whittaker et al. |
| 2006/0025705 A1 | 2/2006 | Whittaker et al. |
| 2006/0030864 A1 | 2/2006 | Kennedy, II et al. |
| 2006/0142732 A1 | 6/2006 | Karmarkar et al. |
| 2006/0167418 A1 | 7/2006 | Khayal et al. |
| 2006/0265043 A1 | 11/2006 | Mandrusov et al. |
| 2006/0282151 A1 | 12/2006 | Weber |
| 2007/0060847 A1 | 3/2007 | Leo et al. |
| 2007/0156114 A1 | 7/2007 | Worley et al. |
| 2007/0156131 A1 | 7/2007 | Datta |
| 2007/0156133 A1 | 7/2007 | McDaniel et al. |
| 2007/0219465 A1 | 9/2007 | Cedro |
| 2007/0282303 A1 | 12/2007 | Nash et al. |
| 2008/0009745 A1 | 1/2008 | Hossack et al. |
| 2008/0086047 A1 | 4/2008 | McDaniel et al. |
| 2008/0097499 A1 | 4/2008 | Nash et al. |
| 2008/0167524 A1 | 7/2008 | Goldwasser et al. |
| 2008/0172037 A1 | 7/2008 | Huang et al. |
| 2008/0208240 A1 | 8/2008 | Paz |
| 2008/0234547 A1 | 9/2008 | Irion et al. |
| 2008/0234661 A1 | 9/2008 | Hastings et al. |
| 2008/0275536 A1 | 11/2008 | Zarins et al. |
| 2008/0287945 A1* | 11/2008 | Schaer ............... A61B 18/1492 606/41 |
| 2008/0312712 A1 | 12/2008 | Penner |
| 2008/0312725 A1 | 12/2008 | Penner |
| 2009/0005754 A1 | 1/2009 | Soetermans |
| 2009/0043299 A1 | 2/2009 | Racz |
| 2009/0082723 A1* | 3/2009 | Krogh ............... A61B 1/00078 604/95.05 |
| 2009/0099420 A1 | 4/2009 | Woodley et al. |
| 2009/0105814 A1 | 4/2009 | Groothuis et al. |
| 2009/0105815 A1 | 4/2009 | Krever et al. |
| 2009/0105816 A1 | 4/2009 | Olsen et al. |
| 2009/0137953 A1 | 5/2009 | Fischer et al. |
| 2009/0149848 A1 | 6/2009 | Werneth et al. |
| 2009/0163822 A1 | 6/2009 | Doan |
| 2009/0171278 A1 | 7/2009 | Hirszowicz et al. |
| 2010/0004627 A1 | 1/2010 | Ludwig et al. |
| 2010/0030114 A1 | 2/2010 | Nguyen et al. |
| 2010/0057037 A1 | 3/2010 | Webler |
| 2010/0063478 A1 | 3/2010 | Selkee |
| 2010/0063479 A1 | 3/2010 | Merdan |
| 2010/0076408 A1 | 3/2010 | Krever et al. |
| 2010/0094334 A1 | 4/2010 | Krever et al. |
| 2010/0164137 A1 | 7/2010 | Selkee |
| 2010/0168666 A1 | 7/2010 | Tegg |
| 2010/0198049 A1 | 8/2010 | Karmarkar et al. |
| 2010/0204560 A1 | 8/2010 | Salahieh et al. |
| 2010/0217261 A1 | 8/2010 | Watson |
| 2010/0226903 A1 | 9/2010 | Morris et al. |
| 2010/0280449 A1 | 11/2010 | Alvarez et al. |
| 2010/0286626 A1 | 11/2010 | Peterson et al. |
| 2010/0312096 A1 | 12/2010 | Guttman et al. |
| 2010/0312178 A1* | 12/2010 | Olsen ............... A61M 25/0133 604/95.04 |
| 2011/0028826 A1 | 2/2011 | Kim et al. |
| 2011/0054465 A1 | 3/2011 | Werneth et al. |
| 2011/0060331 A1 | 3/2011 | Ibrahim et al. |
| 2011/0087112 A1 | 4/2011 | Leo et al. |
| 2011/0087175 A1 | 4/2011 | Krishnan et al. |
| 2011/0130750 A1 | 6/2011 | Ormsby et al. |
| 2011/0166455 A1 | 7/2011 | Cully et al. |
| 2011/0190784 A1 | 8/2011 | Hastings et al. |
| 2011/0213300 A1 | 9/2011 | McWeeney et al. |
| 2011/0224784 A1 | 9/2011 | Quinn |
| 2011/0245842 A1 | 10/2011 | Doan et al. |
| 2011/0251519 A1 | 10/2011 | Romoscanu |
| 2011/0264011 A1 | 10/2011 | Wu et al. |
| 2012/0010490 A1 | 1/2012 | Kauphusman et al. |
| 2012/0046666 A1 | 2/2012 | Klein |
| 2012/0053419 A1 | 3/2012 | Bloom |
| 2012/0071870 A1 | 3/2012 | Salahieh et al. |
| 2012/0109079 A1 | 5/2012 | Asleson et al. |
| 2012/0111482 A1 | 5/2012 | Grunewald et al. |
| 2012/0116199 A1 | 5/2012 | De La Rama et al. |
| 2012/0116200 A1 | 5/2012 | Roy et al. |
| 2012/0130217 A1 | 5/2012 | Kauphusman et al. |
| 2012/0130218 A1 | 5/2012 | Kauphusman et al. |
| 2012/0143099 A1 | 6/2012 | Daniels et al. |
| 2012/0143177 A1 | 6/2012 | Avitall |
| 2012/0190927 A1 | 7/2012 | Uihleim |
| 2012/0203169 A1 | 8/2012 | Tegg |
| 2012/0232563 A1 | 9/2012 | Williams et al. |
| 2012/0239002 A1 | 9/2012 | Griswold |
| 2012/0277730 A1* | 11/2012 | Salahieh ............ A61B 1/00135 604/527 |
| 2013/0116705 A1 | 5/2013 | Salahieh et al. |
| 2013/0204096 A1 | 8/2013 | Ku |
| 2014/0107623 A1 | 4/2014 | Salahieh et al. |

FOREIGN PATENT DOCUMENTS

| | | |
|---|---|---|
| EP | 1 525 897 | 4/2005 |
| JP | 2010/119707 | 6/2010 |
| WO | 2011/33783 | 3/2011 |
| WO | 2012/027383 | 3/2012 |
| WO | 2012/096816 | 7/2012 |

OTHER PUBLICATIONS

PCT/US2013/069470 International Search Report (dated Nov. 11, 2013).

The Extended European Search Report Application No. 13853310.4 dated Jul. 1, 2016.

* cited by examiner

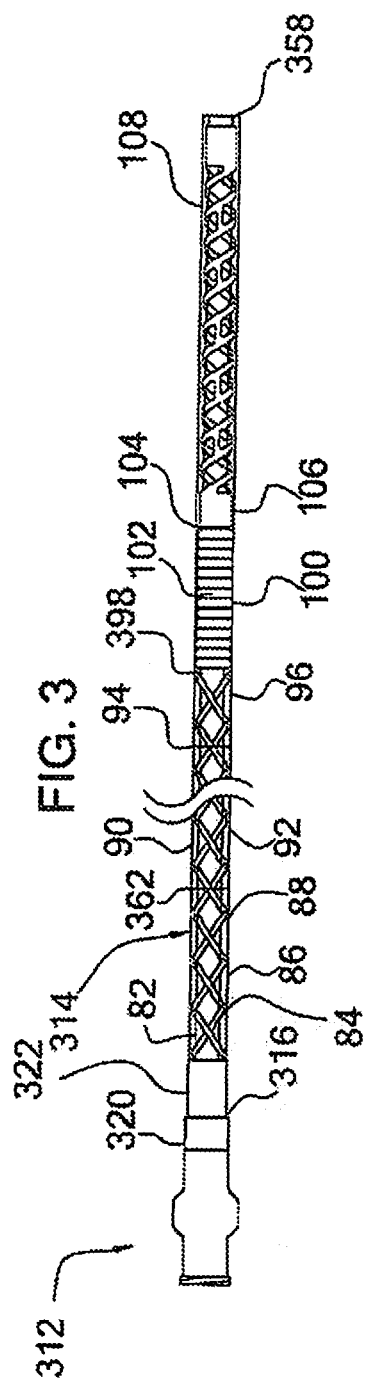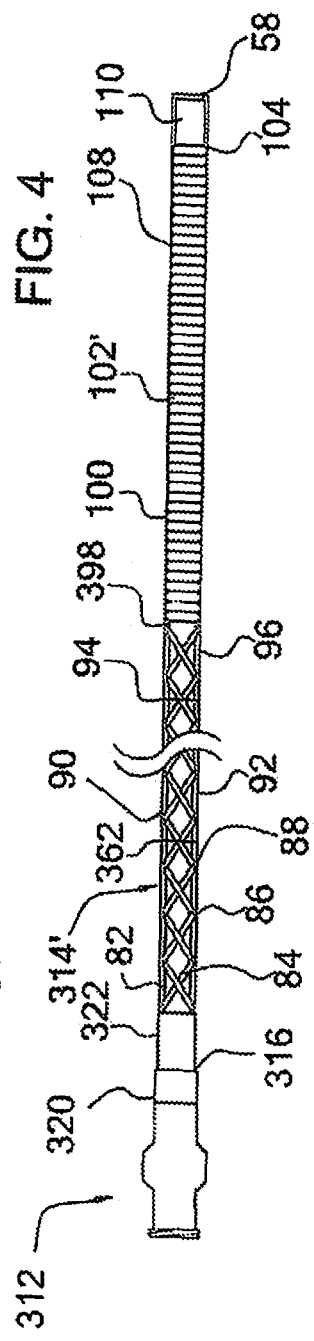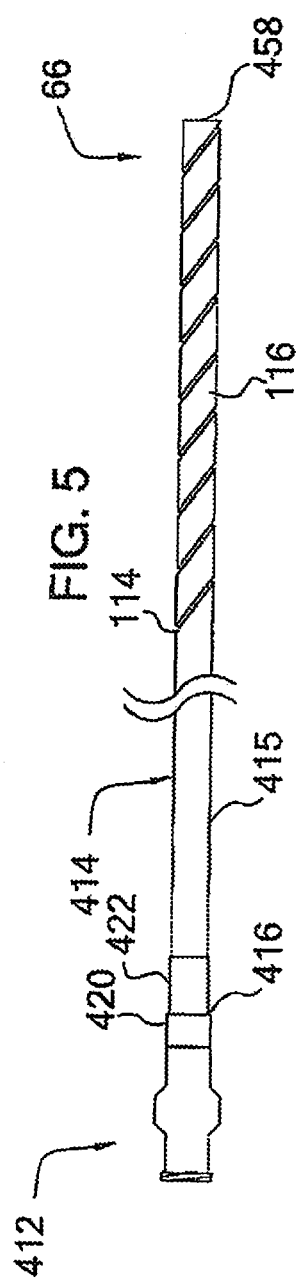

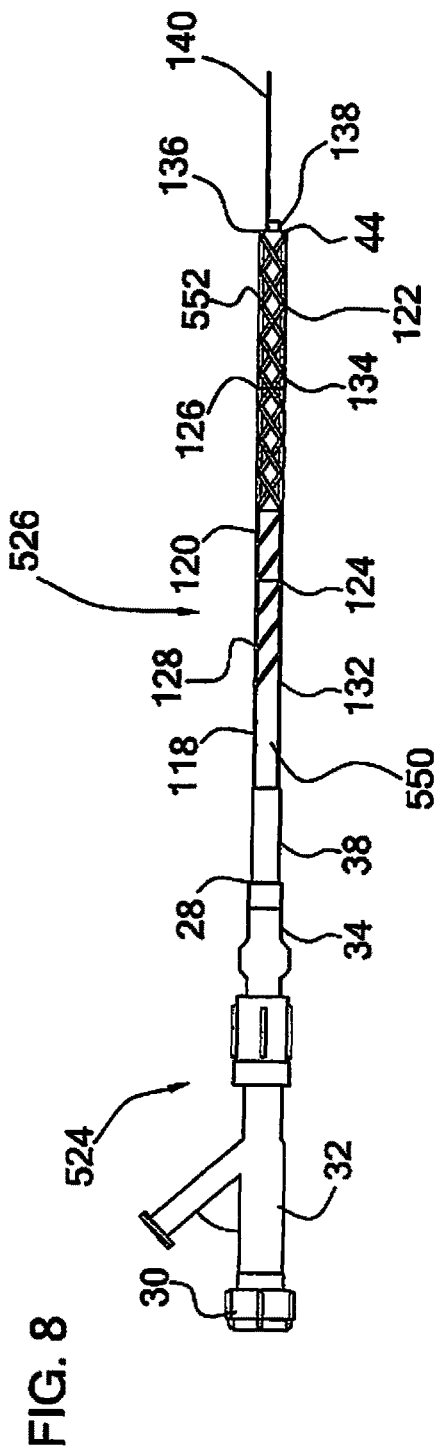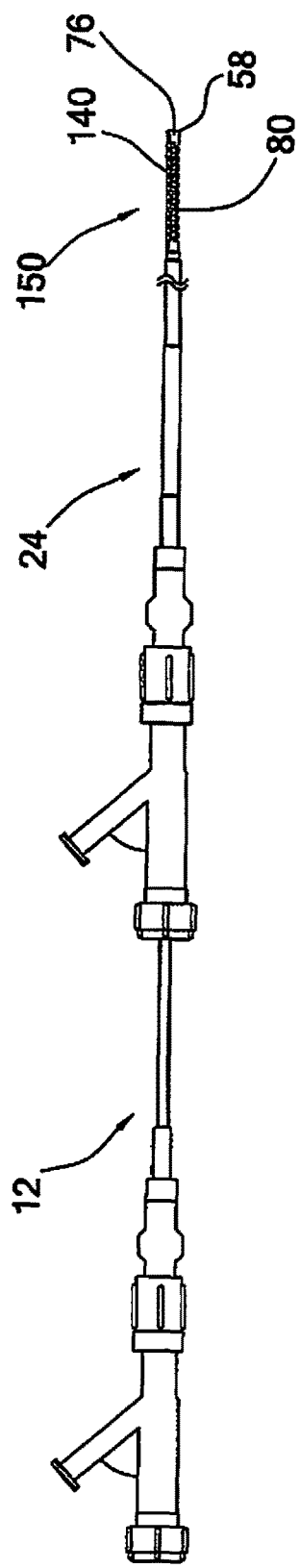
FIG. 8
FIG. 9

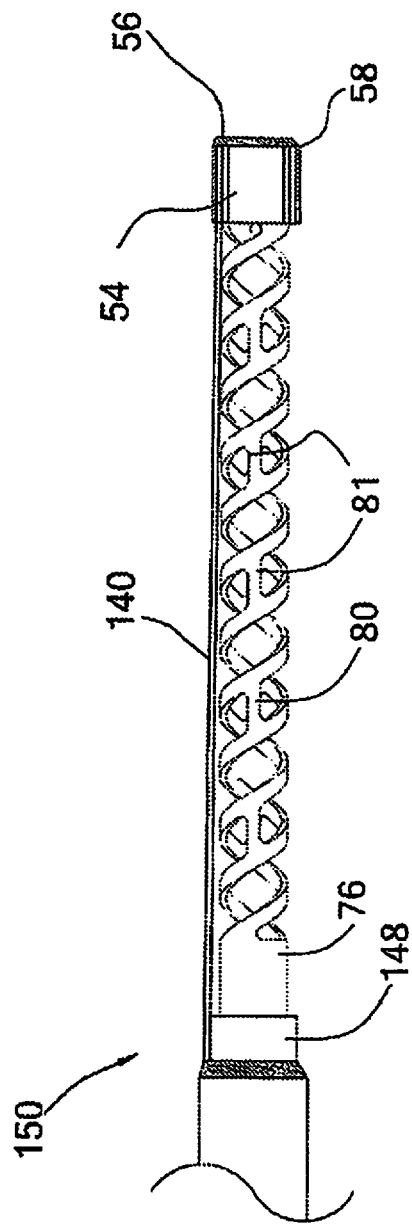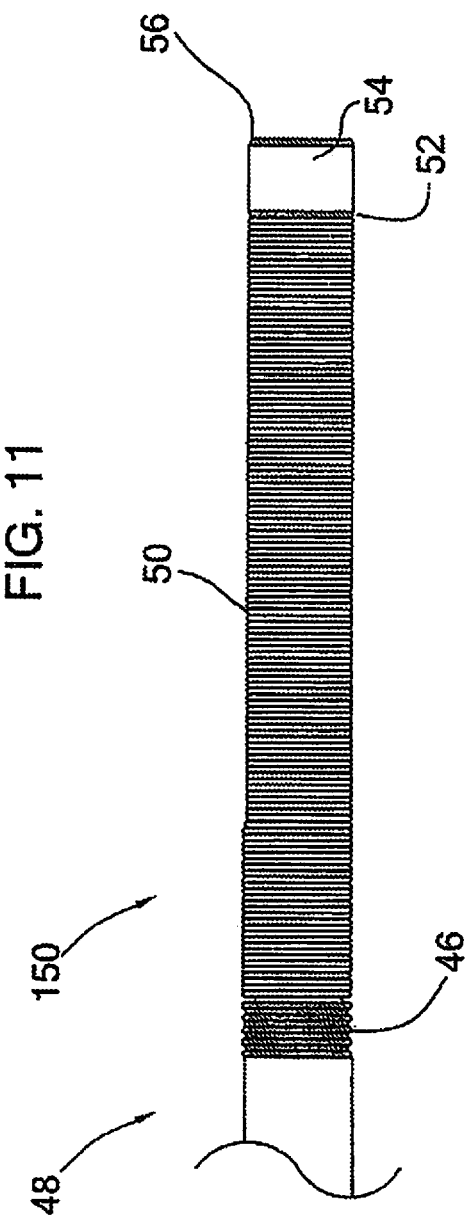

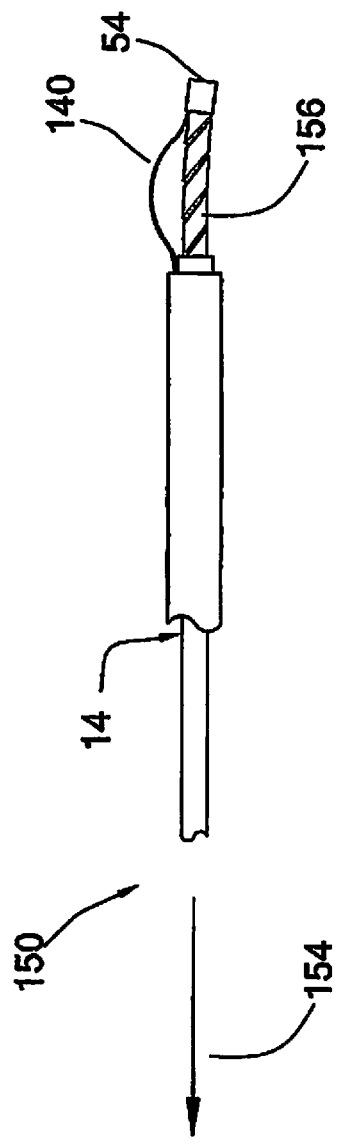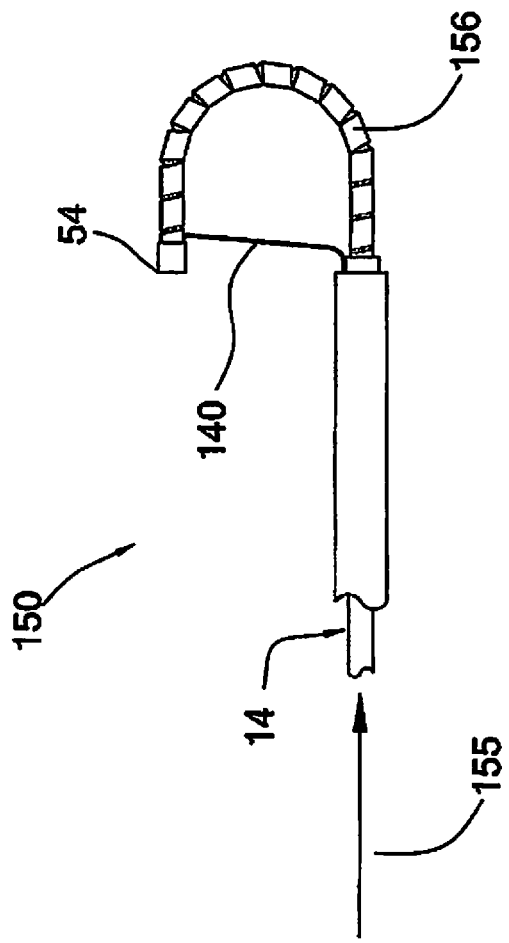
FIG. 12A
FIG. 12B

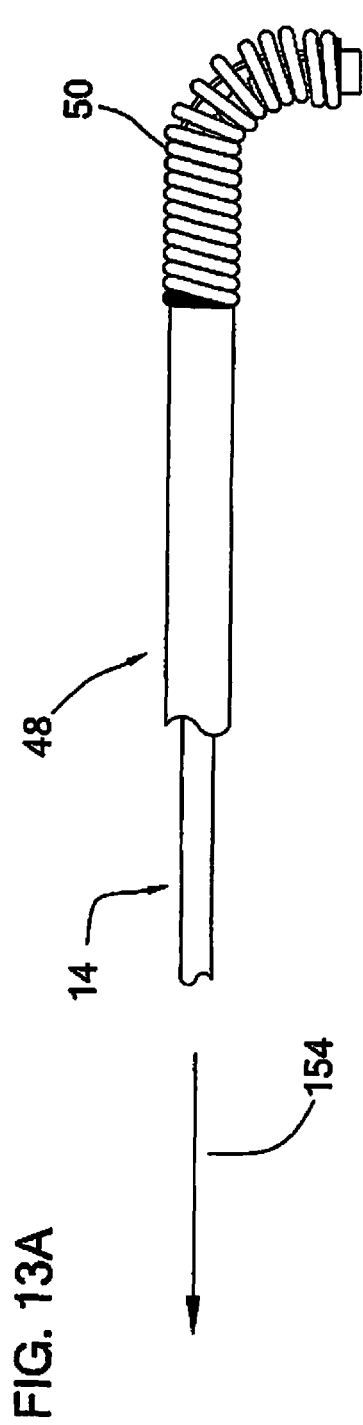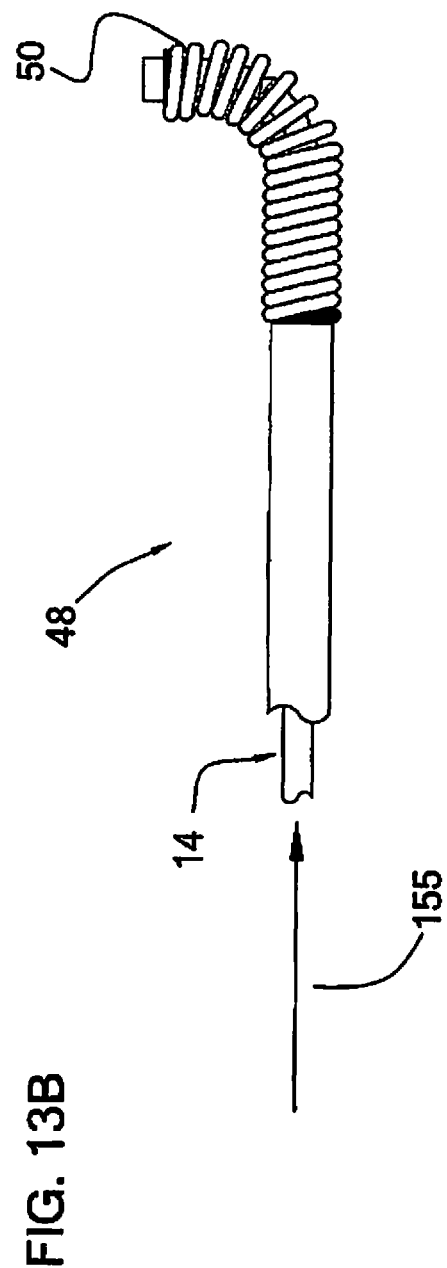
FIG. 13A
FIG. 13B

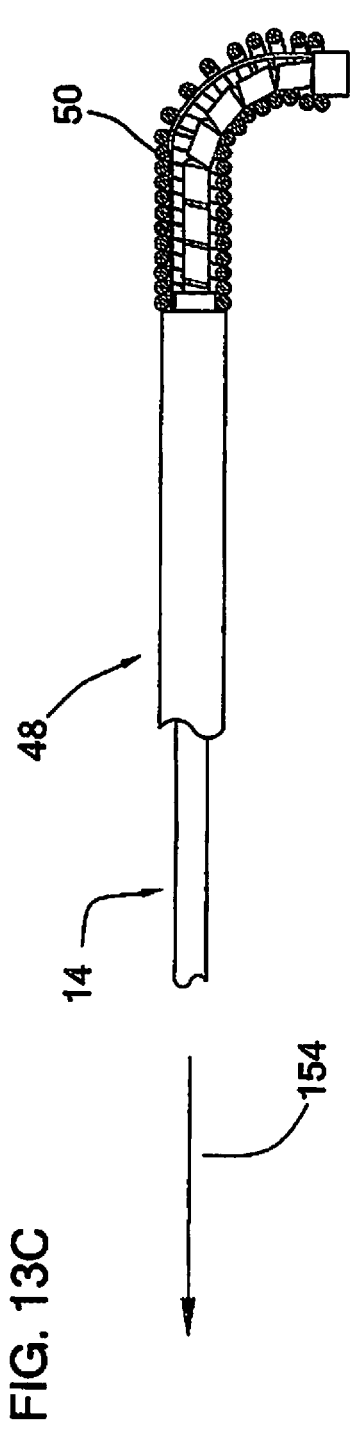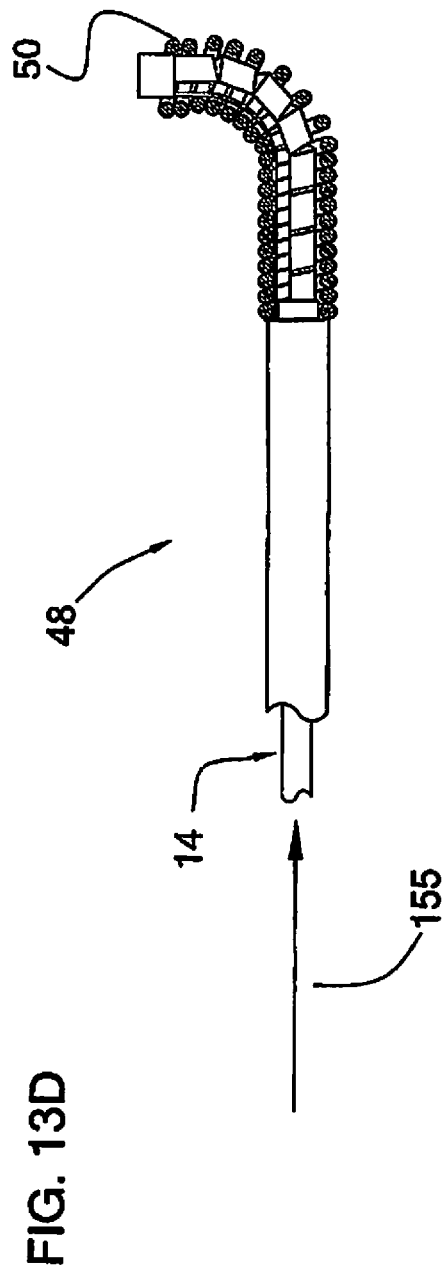
FIG. 13C
FIG. 13D

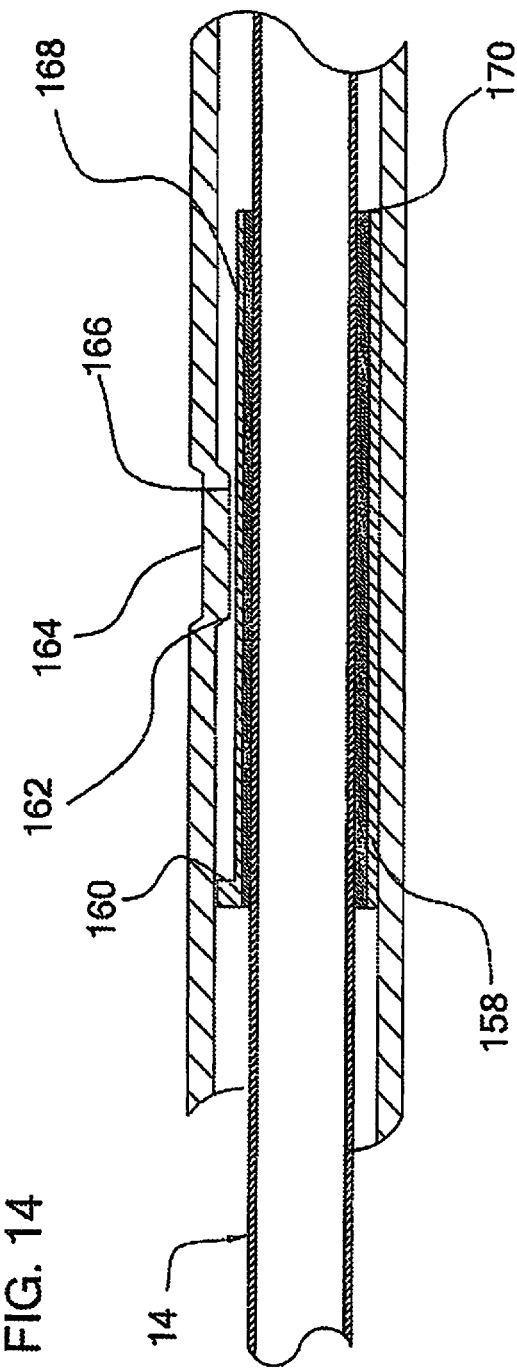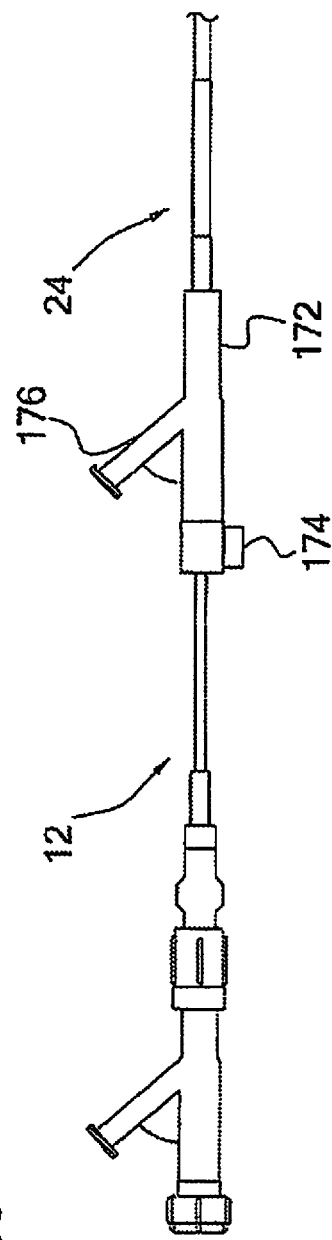

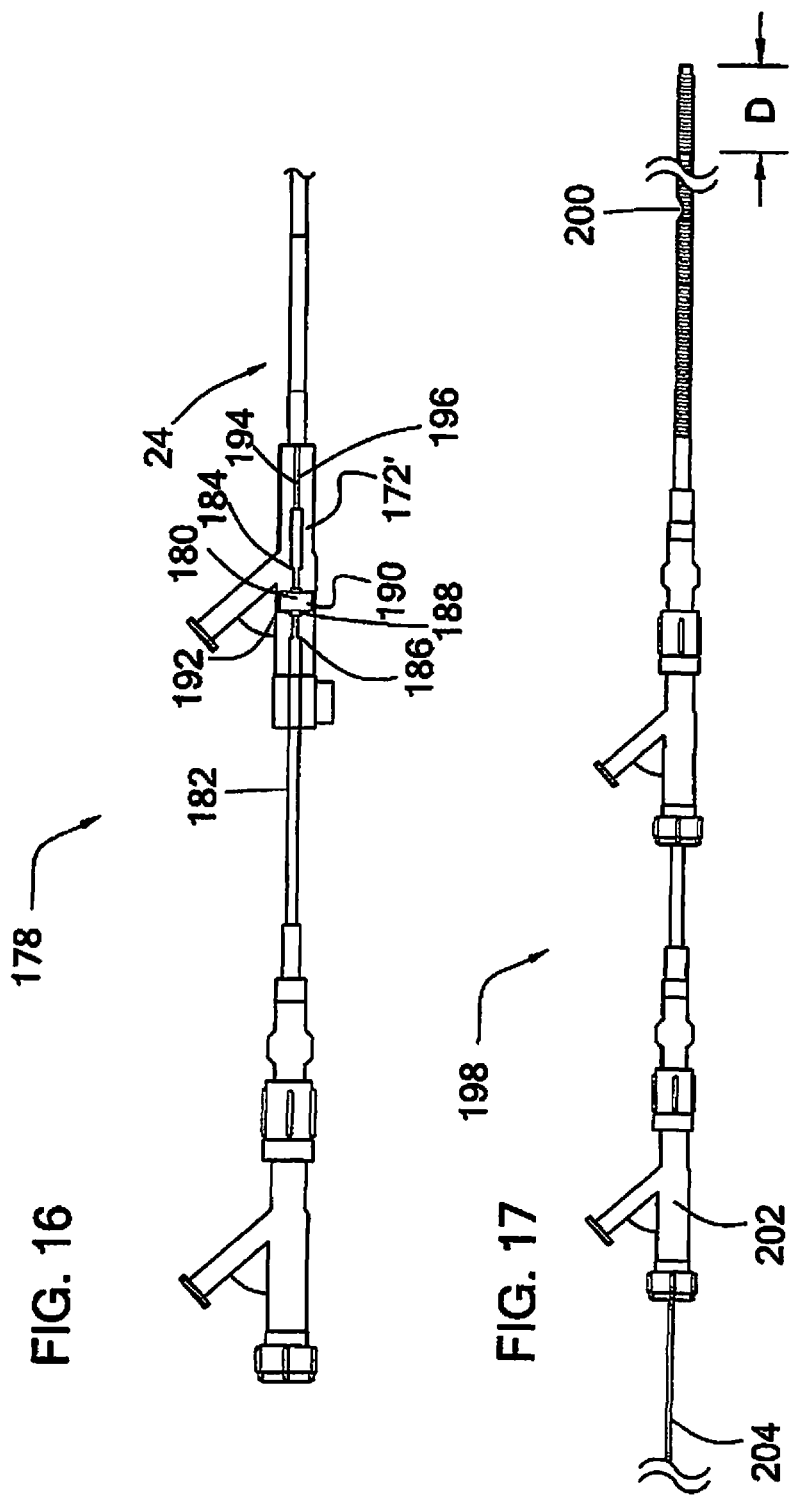

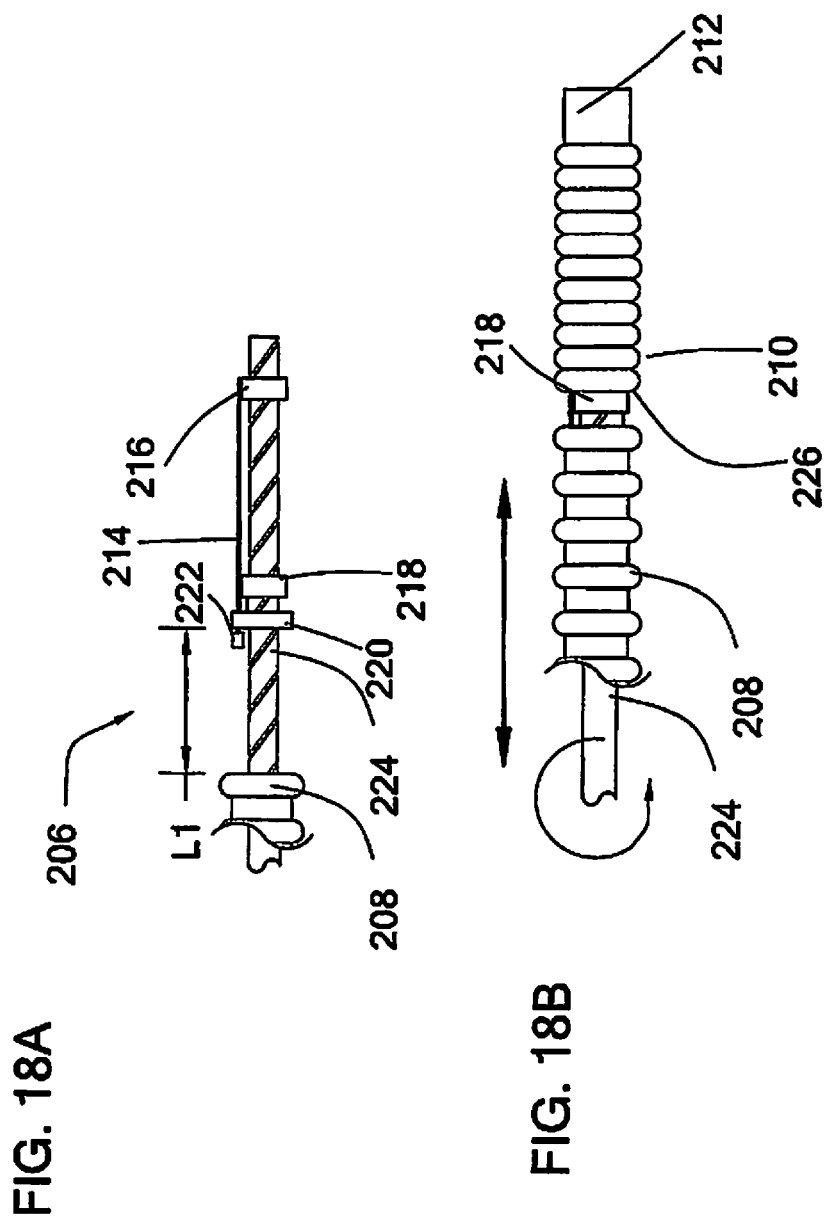

COAXIAL BI-DIRECTIONAL CATHETER

This application is a continuation of application Ser. No. 15/055,553, filed Feb. 27, 2016, which is a continuation of application Ser. No. 14/846,671, filed Sep. 4, 2015, which is a divisional of application Ser. No. 14/064,170, filed Oct. 27, 2013, now U.S. Pat. No. 9,233,225, which claims priority from provisional application Ser. No. 61/724,921, filed Nov. 10, 2012. The entire contents of each of these applications are incorporated herein by reference.

BACKGROUND

Technical Field

This application relates to medical devices, and more particularly, to medical catheters with steering capabilities for use in tracking tortuous pathways or deflecting and/or placing accessories.

Background of Related Art

The concept of a variable stiffness microcatheter for use in navigating into tortuous narrow vasculature for delivery of treatment options such as fluid injection or coil placement is disclosed in U.S. Pat. No. 4,739,786, to Engelson. This is achieved by steam shaping the variable stiffness catheter's distal tip and tracking the catheter in combination with a guidewire, straight or curved. While this method allows for quick, accurate access to remote areas such as those in the brain, it does not allow for slight distal tip adjustments to aid in treatment once the destination site is reached. If adjustments are needed, the catheter or the guidewire, or in some instances both, would have to be removed and re-shaped.

U.S. Pat. No. 6,726,700, to Levine, and U.S. Pat. No. 7,591,813, to Levine et al., attempted to correct this shortcoming by disclosing a microcatheter with a deflectable distal tip. Levine describes a co-linear catheter comprising a flexible joint or hinge region defining a main lumen, used for delivery of guidewires and accessories, and a wire lumen that contains a push/pull wire, which is secured to the distal tip with a radiopaque band. Flexion, or bending, of the hinge region is achieved through remote manipulation of the push/pull wire. While this design might work well on a laboratory bench top or in straight vasculature, it fails to consistently deflect in narrow, tortuous anatomy due to its co-linear design featuring the push/pull wire/hinge construction and the inability to introduce fluid into the wire lumen to act as a lubricant to aid in reducing friction between the movable push/pull wire and the wire lumen.

Both of the Levine patents disclose a co-linear, dual lumen (main lumen and wire lumen) deflectable catheter with tip deflection that is brought about through manipulation of a push/pull wire residing in the wire lumen which cannot be lubricated with fluid. Neither of the above mentioned devices disclose a coaxial (inner catheter and outer catheter) device that uses manipulation of the main lumen (inner catheter) and lubrication to bring about smooth, consistent deflection needed to aid in navigation along a small diameter tortuous pathway and to allow for slight tip adjustments to ensure accuracy in delivering fluids and accessories upon arrival at the desired site, as disclosed herein.

SUMMARY

The present invention provides a coaxial bi-directional deflectable catheter which overcomes the above discussed limitations in tip manipulation in narrow, tortuous anatomy.

The present invention provides in one aspect a deflectable catheter comprising an outer member having a proximal portion and a distal portion, an elongated column member extending distally from the outer member, and an inner member positioned coaxial with the outer member and attached to the column member. The inner member extends distally of the outer member and has a distal tip portion. A reinforcement member is positioned over the column member to restrict axial movement of the column member such that when one of the inner member or outer member is moved with respect to the other, axial compression of the column member is restricted by the reinforcement member causing the distal tip portion of the inner member to deflect laterally.

In some embodiments, the outer member has a central longitudinal axis and the column member is radially offset with respect to the central longitudinal axis of the outer member.

In some embodiments, the lateral reinforcement member comprises a tube. Preferably, in some embodiments, the tube is a helically wound flexible coil. In some embodiments, the column member is fixedly attached to the outer member and the inner member. In other embodiments, the column member is attached only to the inner member.

The outer member can have a central lumen to receive the inner member and/or the inner member can have a central lumen to receive a guidewire or other accessory. The central lumen of outer member can be lubricated to facilitate movement of the inner member therein to facilitate the deflection.

The column member is preferably non-circular in cross section. In some embodiments, the column member has a proximal portion attached to the distal portion of the outer member and a distal portion attached to the distal portion of the inner member.

The catheter can further include a marker band at the distal portion of the inner member and the column can be attached to the marker band. In some embodiments, a proximal portion of the column member terminates at a distal portion of the outer member.

Preferably, upon movement of the inner member proximally or the outer member distally, the axial compression of the column member is limited by the reinforcement member so it cannot fail axially but instead fails laterally to deflect the distal tip portion.

In some embodiments the catheter includes first and second marker bands on the inner member, and the column member is attached to the first and second marker bands.

A locking assembly can be provided to lock the position of the inner member with respect to the outer member.

The inner member can have a cut tube at its distal end portion to provide flexibility.

In accordance with another aspect of the present invention, the present invention provides a deflectable catheter comprising a proximal portion, an intermediate portion and a deflectable distal tip portion. A first movable member is axially movable from a first position to a second position, wherein the distal tip portion is deflectable by an axial movement of the first member in which the distal tip portion cannot fail axially in compression so it fails laterally causing deflection of the distal tip portion in a first direction.

In some embodiments, the first movable member is positioned within a second member, and the first position is distal of the second position. In other embodiments, the first movable member is positioned over a second movable member and the first position is proximal of the second position. In some embodiments, the first movable member deflects while the second movable member remains substantially stationary. In some embodiments, axial movement in an opposite direction causes a bending of the distal tip portion in the opposite direction.

The present invention provides in accordance with another aspect a deflectable catheter having a deflectable distal tip portion comprising an outer catheter having a lumen, a proximal portion and a distal portion, an elongated member extending distally from the outer member, and an inner catheter positioned coaxially within the inner lumen of the outer catheter and attached to the elongated member, wherein axial movement of one of the outer member and inner member causes the distal tip portion of the catheter to deflect laterally.

In some embodiments, the elongated member is attached to the inner member and is surrounded by a movement restriction member to restrict axial movement of the column member when the outer member or inner member is moved axially relative to the other. Preferably, such axial restriction limits axial compression of the column member upon axial movement in one direction. In some embodiments, a tip of the inner catheter deflects and a tip of the outer catheter does not deflect.

Preferably, movement of the inner catheter in one direction causes axial compression of the elongated member and movement of the inner catheter in a second direction causes bending of the elongated member to cause deflection in a second opposite direction.

In accordance with another aspect of the present invention, a deflectable catheter having a deflectable distal tip portion is provided comprising an outer catheter having a lumen, a proximal portion and a distal portion, an inner catheter positioned coaxially within the inner lumen of the outer catheter and having a distal tip portion extending distally of a distal end of the outer catheter, and a column member attached to the inner catheter, wherein axial movement of one of the outer member and inner member acts on the column member to cause the distal tip portion of the inner catheter to deflect laterally.

In some embodiments, the column member includes a proximal stop contacted by the outer catheter.

The present invention also provides in accordance with another aspect a coaxial bi-directional deflectable catheter which can be lubricated internally through external application to help overcome friction between the inner catheter and the outer catheter while deflecting the distal tip in narrow, tortuous vasculature. In a method for lubricating the deflection lumen formed by the inner diameter of the outer catheter, a syringe filled with fluid can be connected to a side arm. The side arm can be part of a locking assembly, and prior to the procedure, with the locking assembly in a locked position, fluid is injected into the inner lumen of the outer catheter. The locking assembly can then be opened and the inner catheter pulled and pushed to deflect the tip, with the fluid ensuring smooth movement. With the locking assembly locked, the catheter and guidewire can then be inserted and tracked through the anatomy. If, at any point, deflection is impaired, additional lubrication fluid can be introduced through the side arm using a syringe.

BRIEF DESCRIPTION OF THE DRAWINGS

Preferred embodiments of the present disclosure are described herein with reference to the drawings wherein:

FIG. 3 illustrates an inner catheter in accordance with another embodiment of the present invention;

FIG. 4 illustrates an inner catheter of yet another embodiment of the present invention;

FIG. 5 illustrates an inner catheter of still another embodiment of the present invention;

FIG. 8 is a side view of an outer catheter of another embodiment of the present invention;

FIG. 9 illustrates the inner catheter of FIG. 2 positioned inside the outer catheter of FIG. 6 to form the deflectable catheter;

FIG. 10 is an enlarged view of the distal portion of the catheter of FIG. 9 with the lateral reinforcement (support) tube removed to show the column;

FIG. 11 is an enlarged view of the distal portion of the deflectable catheter of FIG. 10 with the lateral reinforcement tube;

FIG. 12A is a side view of the internal structure of the inner catheter of FIG. 5 showing the effect on the column of axial movement of the inner catheter in the proximal direction in the absence of the lateral support tube;

FIG. 12B is an enlarged view of the internal structure of the inner catheter of FIG. 5 showing the effect on the column of axial movement of the inner catheter in the distal direction in the absence of the lateral support tube;

FIG. 13A is an enlarged view showing the effect of axial movement of the inner catheter in the proximal direction in the presence of the lateral support tube;

FIG. 13B is an enlarged view showing the effect of axial movement of the inner catheter in the distal direction in the presence of the lateral support tube;

FIG. 13C is a side partial cutaway view illustrating movement of the column as in FIG. 13A;

FIG. 13D is a side partial cutaway view illustrating movement of the column as in FIG. 13B;

FIG. 14 is an enlarged cross-sectional view of a rotation control member for controlling rotation between the inner catheter and the outer catheter in accordance with an embodiment of the present invention;

FIG. 15 is a side view of a proximal portion of an alternate embodiment of the deflectable catheter having a locking assembly with a side arm for fluid introduction;

FIG. 16 is a side view of an alternate embodiment of a locking assembly for manipulating and locking the distal deflecting tip of the catheter;

FIG. 17 is a side view of an alternate embodiment of the deflectable catheter of the present invention having a rapid exchange port;

FIG. 18A is a side view of another alternate embodiment of the mechanism for deflecting the distal tip of the catheter with the lateral reinforcement tube removed for clarity;

FIG. 18B illustrates the mechanism for deflecting the distal tip of catheter of FIG. 18A with the lateral reinforcement tube shown.

DETAILED DESCRIPTION

The present application provides a bi-directional deflectable catheter with enhanced deflection to enable and facilitate tip deflection in narrow tortuous vasculature. Various embodiments of the deflectable catheter are disclosed herein which include various embodiments of both the inner catheter (inner member) and the outer catheter (outer member) which make up the structure of the microcatheter. The catheter has a deflectable distal tip portion which is deflected due to the arrangement of the inner catheter, outer catheter and column member which is attached to the inner catheter. The column member has a movement restriction member thereover. Relative movement of the outer catheter and inner catheter effects lateral deflection of the distal tip portion due to the restriction member limiting lateral movement of the column. This is explained in more detail below. The structural elements of the catheter and variations thereof will first be described.

Figure 1:
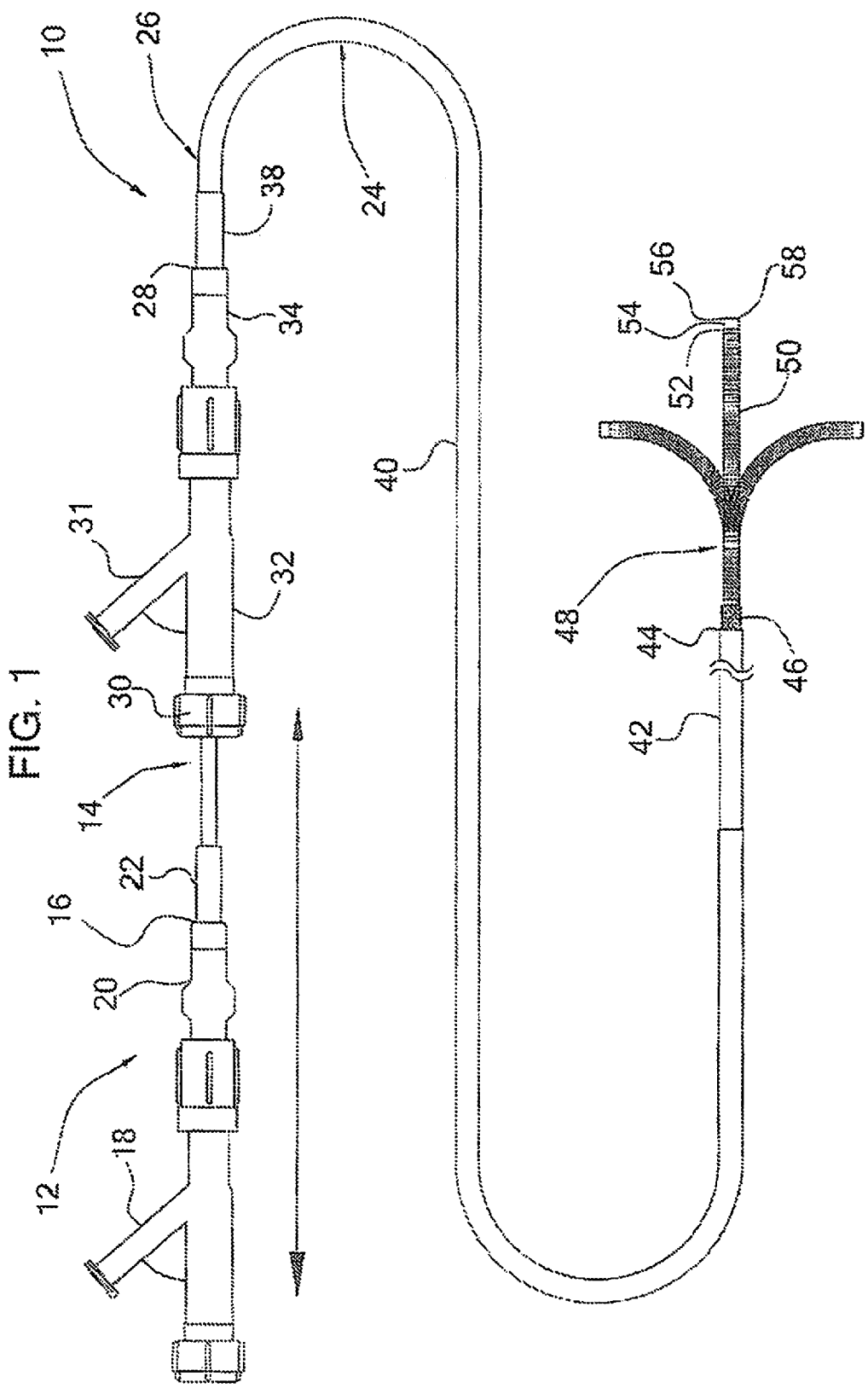
FIG. 1 is a side view of a deflectable catheter of one embodiment of the present invention.

Turning to a first embodiment and with reference to FIG. 1 a bi-directional coaxial deflectable microcatheter is illustrated and designated generally by reference numeral 10. The catheter 10 includes an inner catheter (member) 12, an outer catheter (member) 24 and a distal portion 48 with a deflectable tip.

The inner catheter 12, which extends through a lumen in outer catheter 24, is composed of a catheter body that is constructed of a thin walled body or tube 14 that extends between proximal end 16 and distal end 58 having an inner lumen with a diameter in the range of about 0.001" inches to about 1.993" inches with a preferred inner diameter of about 0.017" inches. Coupled to the proximal end of inner catheter body 14 is winged hub 20, which sits on a strain relief 22 which optionally can be provided. The winged hub (luer) 20 can be made of plastic. If desired, winged hub 20 can also be fitted with a rotating hemostatic valve (RHV) 18 to provide a channel into the inner lumen of inner catheter 12 for insertion of an accessory or fluid introduction through the side arm. Possible accessories may include by way of example: guidewires, coils, fiberscopes, forceps, video cameras, laser or electrohydraulic lithotripsy devices, and illumination or laser fibers. Other accessories can also be inserted through the channel.

Outer catheter 24 is composed of a catheter body that is constructed of a thin walled body or tube 26 having an inner lumen that extends between proximal end 28 and distal end 44 having an inner lumen with a diameter in the range of about 0.007" to about 1.999" with a preferred inner diameter of about 0.027". Outer catheter body 26 also features a relatively stiff proximal section 40 that is joined to a relatively flexible distal section 42. Coupled to the proximal end of outer catheter body 26 is winged hub (luer) 34, which sits on strain relief 38 which optionally can be provided. Attached to winged hub 20 is rotating hemostatic valve (RHV) 32 with end cap 30 and side arm 31. End (lock) cap 30 acts as the locking assembly for the deflectable catheter while side arm 31 is used for introduction of fluids for lubrication and possibly visualization. The lubrication can facilitate relative movement of inner catheter 12 during the procedure which facilitates deflection by ensuring smoother relative movement of the inner and outer catheters. When cap 30 is fully opened, inner catheter 12 is free to move axially resulting in distal tip 48 deflection as described below. Cap 30 can be tightened at any point in the deflection process to clamp and hold inner catheter 12 in position and thereby lock the tip 48 in place.

Deflectable tip 48 of inner catheter 12 is covered with lateral support tube 50, which overlies the column member described below. Support tube 50 is adhered at its proximal and distal ends 46 and 52, respectively, as shown in FIG. 11 and described below. Preferably lateral support tube 50 is a helically wound flexible coil with an outside diameter in the range of about 0.008" to about 2.00" with a preferred diameter of about 0.034". The coil may be made from a polymer or metal material but the preferred material is platinum/iridium for radiopacity. Disposed distally of lateral support tube 50 is marker band 54, which is adhered at end 56 to the distalmost end 58 of the inner catheter 10. The band 54 can be made from a polymer or metal, the preferred material is platinum/iridium for radiopacity.

Figure 2:
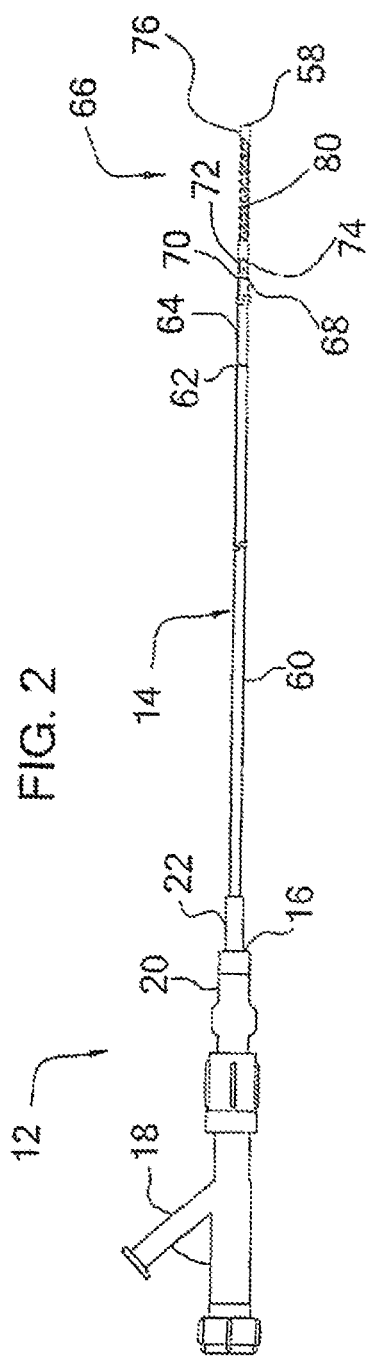
FIG. 2 is a side view of one embodiment of an inner catheter of the deflectable catheter of FIG. 1.
Figure 2A:
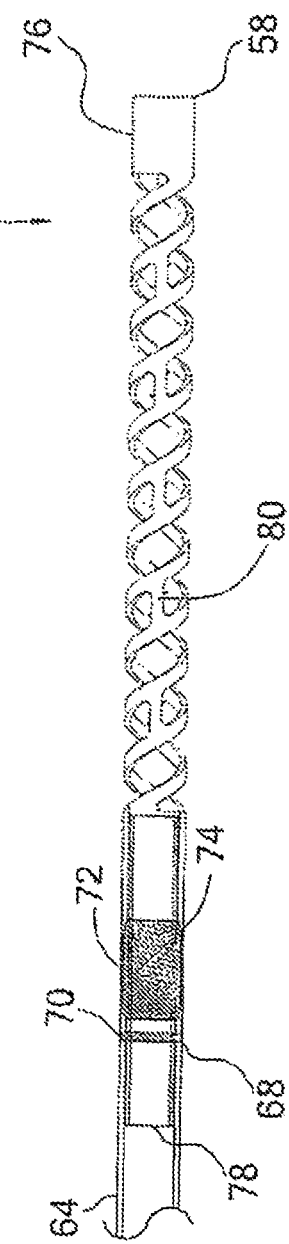
FIG. 2A is an enlarged view of the distal portion of the inner catheter of FIG. 2.

FIGS. 2 and 2A illustrate one embodiment of inner catheter 12 of deflectable catheter 10. The inner catheter 12 as discussed above includes a winged hub 20, which sits on an optional strain relief 22 and optional RHV 18. Inner catheter 12 also includes catheter body 14 which preferably has a stiff proximal section 60 made up of a braid reinforced polymer tube that has an outer diameter in the range of about 0.002" to about 1.994" with a preferred diameter of about 0.023" and a length that extends between proximal end 16 and distal end 62 in the range of about 0.5 inches to about 34 feet with a preferred length around 110 cm. Proximal section 60 is coupled at a distal end to a less stiff distal tube 64 that can be made of a braid or coil reinforced polymer but is preferably made up of high density polyethylene (HDPE) that has an outer diameter in the range of about 0.002" to about 1.994" with a preferred diameter of about 0.022" and length that extends from a proximal end (adjacent distal end 62 of proximal section 60) to distal end 68 in the range of about 0.5 inches to about 34 feet with a preferred length around 45 cm. The overall usable length for the combined proximal and distal sections has a range of about 0.5 inches to about 34 feet with a continuous inner diameter in the range of about 0.001" to about 1.993" with a preferred useable length being approximately 150 cm and with a preferred inner diameter of about 0.017". Inner catheter body 14 further includes laser cut tube 76, with window 74, which is coupled to distal tube 64 at its distal end 70. Laser cut tube 76 can be made of plastic or metal but is preferably made of super elastic nitinol with an inner diameter in the range of about 0.001" to about 1.993" with a preferred diameter of about 0.017". The outer diameter for laser cut tube 76 can range from about 0.002" to about 1.994" with a preferred outer diameter of about 0.022". The length of the laser cut tube can range from about 0.5 inches to about 34 feet with a preferred length of approximately 1 cm.

Distal portion 66 of inner catheter body 14 includes laser cut tube 76 that is coupled to distal tube 64 using a tube 78, which is preferably a polyimide tube coated with adhesive 72. Preferably polyimide tube 78 has an inner diameter in the range of about 0.001" to about 1.993" with a preferred inner diameter of about 0.0165". The outer diameter of polyimide tube 78 can range from about 0.002" to about 1.994" with a preferred diameter of about 0.0175". Preferably, the length of polyimide tube 78 can range between about 0.25 mm and about 1 cm with a preferred length of approximately 3 mm.

The overall useable length of the inner catheter 12, which ranges from about 0.5 inches to about 34 feet, need not have separate materials for all of the sections (proximal, distal, and laser cut tube) described above. For instance, a laser cut nitinol tube (or other metal or plastic material such as polyimide) can have the necessary stiffness variations for the proximal and distal sections designed into it resulting in a suitable inner catheter body that meets the ranges for inner catheter 14.

FIG. 3 illustrates an alternate embodiment of the inner catheter designated by reference numeral 312. In this embodiment, the inner catheter body 314 has a lubricious inner liner 82 that runs from proximal end 316 to distal end 358. The purpose of the liner is to help reduce the coefficient of friction to aid in guidewire movement within the inner catheter 314. The liner can be made of materials such as polytetrafluoroethylene (PTFE) or fluorinated ethylene propylene (FEP).

The liner 82 is topped with a combination of a continuous braid 84, coil 102, and laser cut tube 106 to help with lumen integrity (reinforcement) and to aid in stiffness variation. The braid 84, which can be made of flat or round wire or a combination, runs from proximal end 316 to distal end 398. The braid can be made of materials such as stainless steel, nitinol, polymer, fiber or even a combination of materials. The coil 102, which can be made of flat or round wire, runs from proximal end 398 to distal end 104. The coil 102 can be made of materials such as stainless steel, nitinol, platinum/iridium or even a polymer. The laser cut tube 106 runs from proximal end 104 just about to distal end 358. Laser cut tube 106 can be nitinol or other metal or it can be cut from polyimide as done by MicroLumen (Oldsmar, Fla.) or another polymer.

The reinforcement layer is topped with polymers with varying stiffnesses to create three distinct sections: proximal section 86, mid section 90, and distal section 96. Proximal section 86 extends distally from proximal end 316 to distal end 362. Mid section 90 extends distally from end 362 to distal end 94. Distal section 96 extends from end 94 to distal end 358. The stiffness will decrease from proximal section 86 to distal section 96. Reduction in stiffness can be achieved by using decreasing durometers of material from proximal to distal. Preferably, proximal section 86 can be formed using material 88 which can be a nylon or pebax having a durometer in the range of 60 D to 75 D or any other material having a relative durometer hardness value of around 72 D, mid section 90 can be formed using a lower hardness material 92 with a durometer of around 63 D, and distal section 96 can be formed with an even lower hardness material 100 such as a pellethane material having a durometer of 25 D to 55 D or other material having a durometer between 25 D and 40 D. These are just examples of materials and durometers that can be used. Also, each section does not need to be formed with a single layer of material, if desired, sections can be constructed of two or more layers. Actual material selection will be based on design needs for flexibility and stiffness. Additional layers of coils or braids may also be added as needed.

These layers are then fused together using a re-flow process (heat). Strain relief 322 and winged hub 320 are then added. Lastly, the inner catheter may optionally be coated on its outer diameter for a length with a hydrophilic coating 108. The purpose of the coating is to aid in axial movement of the inner catheter relative to the outer catheter during the deflection process. If the coating requires hydration, liquid can be injected through the side arm 31 on RHV 32 attached to outer catheter 10 (see FIG. 1).

As stated above, the typical microcatheter is formed using a re-flow technique which fuses all of the layers together with heat and, if necessary removable heat shrink tubing. As the length of the inner catheter (or outer catheter) increases to greater than 180 cm this may be a problem due to current equipment restrictions. An alternate method is to use non-removable heat shrink tubing of varying stiffness to create the proximal, mid, and distal sections. Also, although FIG. 3 shows the braid 84, coil 102, and laser cut tube 106 stopping or starting in either the proximal, mid, or distal section, each of those components can be made longer or shorter and as a result end or start at points different than shown.

FIG. 4 illustrates another embodiment of the inner catheter designated generally by reference number 312. Construction of inner catheter body 314' is much the same as that of FIG. 3 with the exception of a longer, continuous coil 102' for the laser cut tube 106. A marker band 110 is provided. The marker band 110 may be made of platinum/iridium to aid in visualization under fluoroscopy or of other metals or plastics. The band 110 can also be made from a coil rather than a solid tube as shown or even omitted from the design. The remaining structure of the catheter is the same as in FIG. 3 and therefore identical reference numerals are used to identify identical parts.

Another embodiment of the inner catheter is shown in FIG. 5. In this embodiment, the inner catheter body 412 is made from a single stainless steel or nitinol hypotube (or alternatively a plastic or polyimide) that has a laser cut spiral section 116 that extends from proximal end 114 (adjacent distal section 415) to distal end 458. If needed, the proximal end of the inner catheter body 414 can have texturing, such as axial knurling, contouring, or even additional layers or perpendicular features added to aid in pushing/pulling and locking. The catheter 412 includes strain relief 422 and winged hub 420 at proximal 416. As in other embodiments, an optional outer shrink tubing or polymer layer and/or an inner lubricious layer can be added to the embodiment of FIG. 5 to restrict stretching or misalignment of the spiral coil due to axial movement and bending.

Figure 6:
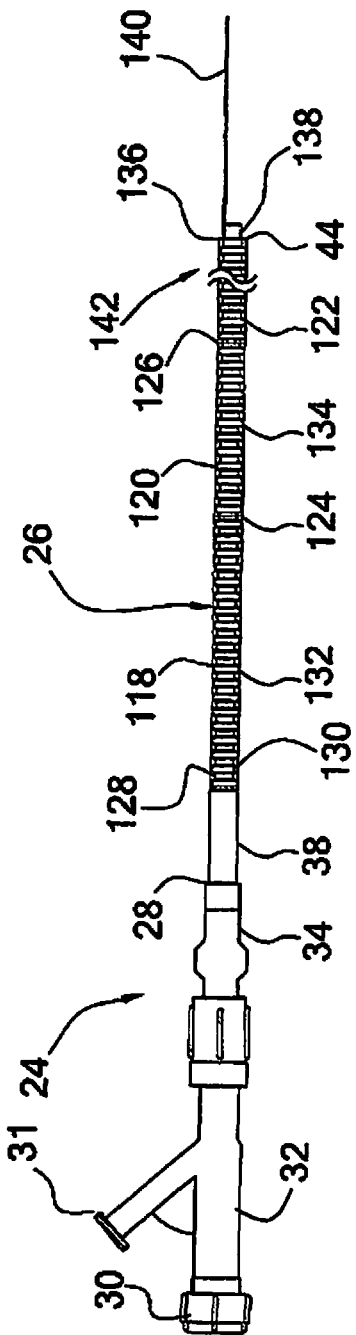
FIG. 6 is a side view of one embodiment of the outer catheter of the deflectable catheter of FIG. 1.

Turning now to the outer catheter structure of the microcatheter, and with initial reference to FIG. 6, this Figure illustrates one embodiment of outer catheter 24 of deflectable catheter 10. In this embodiment, as noted above, outer catheter body 26 has RHV 32 with locking cap 30 and side arm 31 attached to winged hub 34. Winged hub 34 sits on strain relief 38, both of which are coupled to catheter body 26.

Outer catheter body 26 has a lubricious liner 128 that runs from proximal end 28 to distal end 44 and has an inner diameter with a range of about 0.007" to about 1.999" and a preferred inner diameter of approximately 0.27". The purpose of the liner 128 to is aid in movement of the inner catheter during the deflection process by reducing the coefficient of friction between the outer catheter inner diameter and the inner catheter outer diameter. The liner can be made of materials such as polytetrafluoroethylene (PTFE) or fluorinated ethylene propylene (FEP).

The liner 128 is topped with a reinforcement layer of a continuous open pitch coil 130 that runs from proximal end 28 to distal end 44. The coil 130 can be made of flat or round wire. The coil 130 can be made of materials such as stainless steel, nitinol, platinum/iridium or even a polymer or fiber. Also, the coil 130 need not be open pitch or a continuous length for the entire length of outer catheter body 26. For instance, the distal end may need to have a certain length of radiopacity and therefore require a platinum/iridium coil. To keep cost low, only the section requiring radiopacity could be platinum/iridium while the remainder of the body could be covered with a lower cost coil, such as a stainless steel version.

The reinforcement layer is topped with polymers with varying stiffnesses to create three distinct sections: proximal section 118, mid section 120, and distal section 122. Proximal section 118 extends distally from proximal end 28 to distal end 124. Mid section 120 extends distally from distal end 124 of proximal section 118 to distal end 126. Distal section 122 extends from distal end 126 of mid section 120 to distal end 44. The stiffness will decrease from proximal section 118 to distal section 122. Reduction in stiffness can be achieved by using decreasing durometers of material from proximal to distal. For instance, proximal section 118 can be formed using material 132 which can be a nylon or pebax having a durometer in the range of 60 D to 75 D or any other material having a relative durometer hardness value of around 72 D, mid section 120 can be formed using a lower durometer material 134 with a durometer of around 63 D, and distal section 122 can be formed with an even lower hardness material 136 such as a pellethane material having a durometer of 25 D to 55 D or other material having a durometer between 25 D and 40 D. These are just examples of durometers that can be used, as actual material selection can be modified to optimize the balance of flexibility and stiffness. The layers that are selected are then fused together using heat. Alternatively, the entire outer catheter body can be made of a single durometer tube from materials such as HDPE, LDPE, nylon polyimide or polyurethane. A lubricious liner and reinforcement coil or braid may optionally be added to this tube as well. If needed, one or more lumens (for delivery or balloon inflation) can then be added in parallel along the length of outer catheter body 26 using adhesive or one or more heat shrink tubings, which may or may not be removed and may have differing durometers. The winged hub 34, strain relief 38, and RHV 32 with locking cap 30 and side arm 31 are then added.

The final useable length for outer catheter 26 can range from about 0.5 inches to about 34 feet with a preferable useable length of about 135 cm. The proximal outer diameter can range from about 0.008" (0.61 Fr) to about 2.00" (152 Fr) with a preferred proximal outer diameter of about 1 mm (3 Fr) and a preferred distal outer diameter of about 0.93 mm (2.8 Fr).

Outer catheter body 26 further includes a marker band 138, which is inserted mid way into the inner diameter at the distal end of outer catheter body 26. Preferably marker band 138 has a length in the range of about 0.005" to about 1" with a preferred length of about 0.039" and an inner diameter in the range of about 0.0065" to about 1.9985" with a preferred inner diameter of about 0.0265". The outer diameter has a range from about 0.0075" to about 1.9995" with a preferred outer diameter of about 0.0285". The marker band 138 can be made of a metal or a polymer tube or coil with a preferred material of platinum/iridium.

The catheter 10 includes an elongated longitudinally extending column member, e.g., a wire or tube, which extends distally of the outer catheter 24, and shown in FIG. 13C as a separate component, is attached to the inner catheter, axially aligned at its ends, and is surrounded by a restriction (support) tube to restrict lateral movement of the column member. In one embodiment the column member includes a column 140, which at its proximal end sits on marker band 138 or alternatively in a slot cut along the length of the marker band 138. The proximal portion of column 140 is also inserted into the inner diameter, i.e., the catheter body wall, at the distal end of outer catheter body 26. Adhesive 146 is then added to secure the parts in place. Preferably column 140 has a substantially rectangular cross section with a thickness in the range of about 0.0005" to about 0.5" with a preferred thickness of approximately about 0.002". The width can range from about 0.0005" to about 1.95" with a preferred width of approximately about 0.005". The column can have a length that ranges from 0.25 mm to 10 cm with a preferred length of approximately 8 mm. The column's preferred cross section is rectangular however other shapes such as oval can be used. A non-circular cross section is preferred to effect bending in a desired direction. In a preferred embodiment, the column is in the form of a substantially rectangular wire or flat ribbon to control the plane of deflection. Also, cuts or other features can be added to the column to influence movement. For example, the spacing and/or number of the cuts will effect movement as it will affect flexibility. The thickness of the walls and the dimensions will also affect flexibility and movement. The column can be made of any metal or metal alloy and even a plastic, however the preferred material is super elastic nitinol. Note the column 140 extends distally from the outer catheter distal end.

Figure 7:
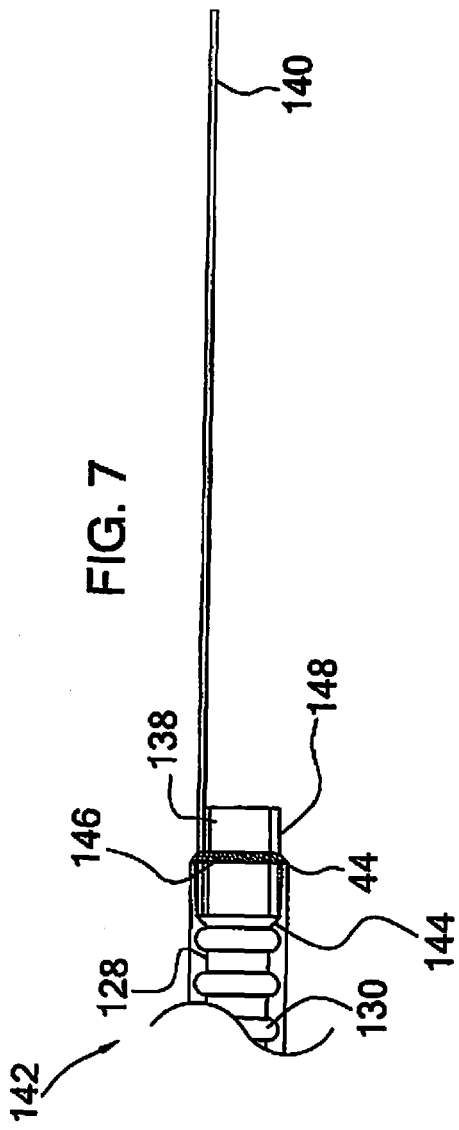
FIG. 7 is an enlarged view of the distal portion the outer catheter of FIG. 6.

Distal portion 142 of outer catheter 24 includes distal end 44 having flare 144 (FIG. 7) so that marker band 138 can be inserted approximately midway into outer catheter body 24 leaving a partial length exposed to create lip 148. Column 140 is then inserted in between lubricious liner 128 and marker band 138 (which may or may not have a slot to accommodate the column) until its proximal end is approximately flush with the proximal end of marker band 138. Adhesive 146 is then applied to join all of the parts.

As an alternative to column 140 and marker band 138 being inserted as two separate parts, the two can be made out of a single nitinol tube (laser cut) if desired or attached as a sub-assembly and then inserted. The band and column assembly may also be added during outer tube manufacture in which case marker band 138 would be slid over a lubricious liner.

An alternate embodiment of the outer catheter of deflectable catheter 10 is illustrated in FIG. 8 and designated by reference numeral 524. In this embodiment, the coil 130 has been replaced by a proximal hypotube 550 with a spiral cut that is butted or attached to the distal braid 552. Lengths for the parts may vary depending on required flexibility and stiffness needed for the part. The spiral cut hypotube 550 can be manufactured from stainless steel, nitinol, polymers or a combination. Likewise, the braid can also be manufactured from stainless steel, nitinol, a polymer, fiber or a combination. The remaining components of catheter 524 are identical to catheter 24 of FIG. 6 and are therefore labeled with the same reference numerals.

By comparing FIGS. 2 through 8 it can be seen that the inner catheter body 14 and outer catheter body 526 can if desired be manufactured using the same materials and methods. Therefore, with the exception of lengths and diameters, it is possible that both structures can be built using a singular design or a mix of the designs presented.

FIG. 9 illustrates inner catheter 12 and outer catheter 24, with column 140 attached, aligned at distal portion 150. In manufacture, inner catheter 12 is inserted into outer catheter 24 until distal end 58 of laser cut tube 76 is flush with the distal end of the column 140. The laser cut tube 76 is then rotated until connectors or ribs 80 are about 90 degrees out of phase with the column 140 (and in a transverse plane and not underneath the column 140) to effect deflection in the desired plane. The distal end alignment can be done before or after rotation for orientation.

Inner catheter 12 and outer catheter 24 are aligned and joined together with marker band 54 and adhesive or solder joint 56 at distal portion 150 (see FIG. 10). Preferably marker band 54 has a length in the range of about 0.005" to about 1" with a preferred length of about 0.039" and an inner diameter in the range of about 0.0065" to about 1.9985" with a preferred inner diameter of about 0.0265". The outer diameter has a range from about 0.0075" to about 1.9995" with a preferred outer diameter of about 0.0285". The marker band can be made of a metal or a polymer tube or coil with a preferred material of platinum/iridium. As one alternate construction, lip 148, column 140, and marker band 54 can all be made out of a single laser cut part made of nitinol, stainless steel or other suitable material. As another alternate construction, column 140 can be soldered to marker band 138 and marker band 54 as a sub-assembly. In another alternate construction, column 140 and laser cut tube 76 can be joined together at the distal ends using a joint formed from solder, glue, laser (depending on material), or other joining process not requiring a band.

The preferred embodiment for alignment of the distal ends of column 140 and the inner catheter 12 (distal ends are approximately flush) is shown in FIG. 10. As an alternative, outer catheter 24 with column 140 attached can be pulled back proximally along inner catheter 12 leaving a portion of the inner catheter body 14 exposed (without column coverage). Marker band 54 can then be slid over the distal end of catheter body 14, i.e., the tube 80, and then over column 140 until its distal edge aligns with the distal end of column 140. Joint 56 can then be formed. This set up will allow the bend radius of the device to remain at approximately half the column length while decreasing the crossing profile of the catheter distal tip to the inner catheter's outer distal tip diameter. Note adjustments may have to be made to the distal tubing 80 (i.e., the laser cut tube) for flexibility and coverage.

FIG. 11 illustrates distal portion 150 with lateral support tube 50 in place which forms a cover for the column to provide the deflection method and system of the microcatheter. Preferably, lateral support tube 50 sits on lip 148 and is a closed pitch helically wound flexible coil made of platinum/iridium with an outer diameter that ranges from about 0.008" to about 2.00" with a preferred outer diameter of about 0.034" and an inner diameter that ranges from about 0.007" to about 1.999" with a preferred inner diameter of approximately about 0.030". The preferred length can range from about 1 mm to about 12 cm with a preferred length of approximately 6.5 mm. The coil may be made of any metal or plastic and may also be open pitched or a combination of open and closed pitch and optionally coated in plastic to form a solid flexible reinforced tube. The lateral tube support (cover) 50 can also be made of a solid tube, that may or may not be laser cut, from plastic materials such as HDPE, LDPE, CFlex, latex, silicone, pebax, nylon, polyurethane or polyisoprene. If solid tubes are used, drainage holes can be introduced on the lateral support tube or even outer catheter body to allow fluid introduced through side arm 31 to exit. The distal portion 150 further includes two joints 46 and 52 that adhere lateral support tube 50 in place. As alternate options, lateral support tube 50 can be made to cover marker band 54 at its distal end or to extend past lip 148 on its proximal end so that it sits directly on outer body 26 of outer catheter 24 or the lateral support tube 50 can be laser cut into the distal end of the outer body 26.

The addition of the lateral support tube 50 and its joints completes the deflectable catheter assembly. At this point, the outer diameter of the catheter can be hydrophilically coated or, if needed, additional lumens (as discussed earlier) for accessories, such as video cameras, fibers optics, or inflatable balloons can be added to the outer shaft. This may be accomplished with adhesives and/or shrink tubing of varying durometers. If attachments are made, the hydrophilic coating would be applied as the final step.

FIG. 12A illustrates distal portion 150 with spiral cut tip 156 (similar to the spiral cut tube of FIG. 5) on the end of inner catheter 12 under an axial pull load in the absence of the lateral support tube 50. When inner catheter body 14 is pulled axially by load 154 in the proximal direction, the internal structure will want to shorten causing column 140 to compress. FIG. 12B illustrates the effect when the inner catheter body is pushed axially by load 155 in the distal direction in the absence of lateral support tube 50. As shown, this applies a moment to the end of the column causing it to bend. Note the load 154 (or 155) required to cause column 140 to move can be increased or decreased by changing the dimensions e.g., cross sectional dimension of column 140. For instance, a stiff column formed for example by a larger cross sectional dimension will require more force to deform and therefore more force to deflect which can in certain instances be more advantageous such as providing more stability to the bent tip.

FIGS. 13A and 13C illustrate distal deflectable tip 48 under axial pull load 154 when lateral reinforcement (support) tube 50 is provided. With lateral support tube 50 in place and axial pull load 154 applied, column 140 can no longer axially compress due to the reinforcement of the column by tube 50. As a result, the entire distal tip, including main (guidewire) lumen, deflects. Note as column 50 cannot be compressed and the tip deflects it moves against the wall. As shown, column 50 bends with tip deflection. As noted above, by varying the dimensions (or materials or cuts) of the underlying column 140, the load 154 to deflect the distal tip can be increased or decreased. However, if the column becomes too thin, the column will become unstable leading to multiple buckling points under load. This will result in little to no tip deflection.

FIGS. 13B and 13D illustrate the effect when the inner catheter body is moved axially by load 155 in the distal direction when lateral support tube 50 is provided. As shown, this bends the distal tip as in FIG. 13B. Note column 50 moves against the wall of the tube 50. As shown, column 50 bends with tip deflection.

Note the movement discussed above and shown in FIGS. 12A-13D is movement of the inner catheter, proximally or distally, respectively, as shown. The same effect is achieved by movement distally or proximally, respectively, of the outer catheter. Movement of both the inner and outer catheters in the desired directions is also contemplated.

A rotation control member 158 for minimizing rotation between the inner catheter 12 and outer catheter 24 can be provided as shown in FIG. 14. Rotation control member 158 is fixedly attached to inner catheter body 14 with joint 170. Flat section 168 on rotation control member 158 works with flat section 166, which is formed by indentation 164 on outer catheter body 26, to control rotation or torquing of the catheters relative to one another. Rotation control member 158 further includes proximal lip 160, which acts as an axial stop when it comes in contact with shoulder 162 on indentation 164. Rotation control member 158 is preferably made of stainless steel but any metal or plastic can be used. The length can have a range from about 1" to about 24 feet with a preferable length around 100 cm. Multiple short rotation members can also be used and placed at various points along the outer diameter of inner catheter body 14. Flat section 166 can also be formed directly on a hypotube, which can double as the proximal shaft for inner catheter body 14.

The microcatheter can include a locking assembly 172 for manipulating and locking the distal deflecting tip as shown in FIG. 15. Engagement of button 174 allows the inner catheter 12 to be pulled or pushed axially relative to the outer catheter 24 resulting in deflection of the distal tip. Once a deflected shape is decided upon, the button is released to set the shape. The button can also be held in (locked) so that the tip can be reshaped freely with catheter advancement. Alternately, the outer catheter 24 can be moved relative to the inner catheter 12 while the button is engaged also bringing about deflection. If lubrication is needed between the inner catheter and outer catheter to assist movement of the inner catheter, fluids such as saline or contrast can be injected through side arm 176 of locking assembly 172. If no lubricant is needed, side arm 176 can be excluded from the design.

An alternate locking assembly for microcatheter 178 is illustrated in FIG. 16. Locking assembly 172 is designed for manipulating and locking the distal deflecting tip and has a rotational control system 180 built in. Rotational control system 180 includes a stainless steel hypotube 182 which overlies the inner catheter body and which has been flattened in a region to create distal stop 184 and proximal stop 186, and ovalized or flattened hypotube 188, which in turn is soldered to stainless steel hypotube 180 which overlies tube 188 for fitting within the RHV housing. The flattened tubes are provided to prevent rotation. Glue 192 is used to lock the hypotube 180 assembly in place inside the housing. The locking assembly is slid over inner catheter body 194 and glued in place. A gap 196 is left distal of the hypotube 182 so that hypotube 182 can be pushed distally to cause deflection. Although the handle has been shown without a screw assembly for locking axial movement of the inner catheter, such an assembly can be added to the proximal handle, if desired.

In use, stainless steel hypotube 182 will be allowed to move proximally and distally axially until stops 184 and 186 are reached. Rotation will be restricted due to flattened region on hypotube 182 and ovalized hypotube 188 through which it freely moves. This rotational control concept can be used on deflectable microcatheter designs with a full length guidewire lumen or deflectable microcatheters with rapid exchange ports. In general, this rotational control design can be used on any design that requires pure axial movement with little or no rotation. In addition, although this design uses flattened hypotubes, the concept can be injection molded into parts such as rotation hemostasis valves (RHV) to quicken manufacturing.

FIG. 17 illustrates a coaxial bi-directional microcatheter 198 with a rapid exchange port 200. The purpose of the rapid exchange port is to allow a guidewire to be placed through the side of the inner lumen of the catheter for tracking. The rapid exchange port may be placed anywhere proximal of the deflecting section (D) of the catheter. The exact placement will depend on bending radius used for design. In some embodiments, the exchange port 200 may be 6 mm from the distal tip although other distances are also contemplated. Also, the length of the rapid exchange port which can be cut on the inner catheter may be longer in some embodiments than the cut on the outer catheter to accommodate deflection with guidewire in place. However, they can also be cut to the same length or the outer catheter can be cut longer than the inner. Because the inner and outer catheters move relative to one another, the rapid exchange ports must also be able to move relative to one another to accommodate deflection. If the guidewire or other device will not be deflected, the rapid exchange port can be placed in deflection section D.

This embodiment allows for introduction of other devices through the proximal end of the device. Shown extending from RHV 202 by way of example is an electrohydraulic lithotripsy (EHL) device 204, as made by Northgate Technologies, Inc. (Illinois). Other possible devices for insertion may include biopsy probes, guidewires or laser fibers, for example.

FIGS. 18A and 18B illustrates an alternate embodiment of the distal tip deflection mechanism 206. The design allows the inner shaft with attached components to rotate and deflect 360 degrees with respect to the outer catheter. This is achieved by not attaching the column to the outer catheter and thus the column does not extend and attach both catheters. A portion L1 of the outer catheter 208, the outer coil 210, and band 212 have been removed in FIG. 18A to show the internal construction. Column 214 is attached to distal band 216 and proximal band 218, as in previous designs; however, a section of the column continues proximally where it passes under band 220 which would be glued in place inside outer catheter 208. Attached at the proximal end of the column is stop 222. This configuration will allow the column to turn with the inner catheter body and attached components when it is torqued.

FIG. 18B illustrates the distal tip deflection mechanism 206 with outer catheter 208, distal outer coil 210 and band 212 in place and in use. The inner catheter 224 can be rotated causing the column, which is now part of the inner catheter, to rotate which allows 360 degree deflection because it can deflect in any plane. When the outer catheter 208 is advanced or the inner catheter 224 retracted, the outer catheter 208 will make contact with end 226 and further movement will cause the tip to deflect. If the outer catheter is pulled proximally or inner catheter 224 is advanced, stop 222 contacts the outer catheter and continued movement will cause the catheter to deflect in opposite direction. (Movement of the inner catheter, back and forth, will also cause deflection).

Figures 19A, 19B:
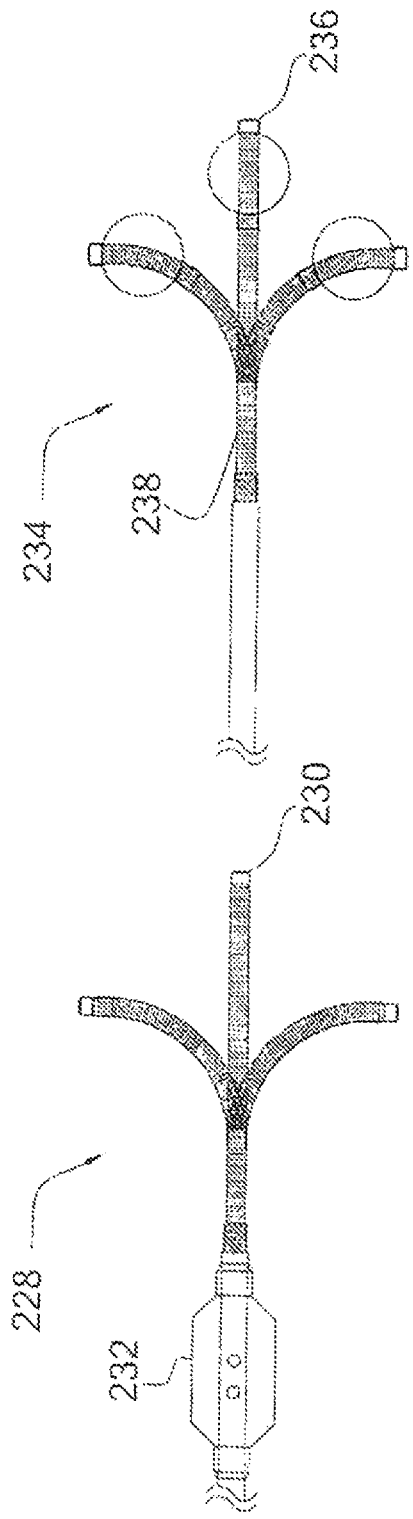
FIGS. 19A and 19B are side views of a distal portion of alternate embodiments of the deflectable catheter of the present invention having a balloon.

In some embodiments, a balloon 232, such as an angioplasty balloon, can be provided on the deflectable microcatheter distal portion. In the embodiment of FIG. 19A, the balloon 232 is mounted proximal of deflecting distal tip 230. In the embodiment of FIG. 19B, distal tip portion 234 of the deflectable microcatheter has balloon 236 mounted distal of deflecting distal tip 238. Other possible options include mounting the balloon in the middle of the deflection zone or at the very distal end, for example.

Note the dimensions and ranges provided herein are given by way example, it being understood that other dimensions and ranges for the components described herein are also contemplated.

The deflection of the catheter of the present invention can be summarized as follows. Bi-directional deflection of the distal tip of a coaxial microcatheter can be broken down into two distinct motions: axial pull deflection and axial push deflection. Axial pull deflection can be modeled as an eccentrically loaded column while axial push deflection can be modeled as an eccentrically loaded beam.

With respect to axial pull deflection, when no lateral support tube is present on the distal end of the catheter, the rectangular nitinol wire (or alternate column member structure such as a rod discussed above) is modeled as an unsupported eccentrically loaded column. This means that when the inner catheter is moved axially proximally with a force P in the proximal direction, the distal end of the column (rectangular nitinol wire) will want to move axially toward its proximal end, resulting in compression (buckling) of the nitinol wire. This is shown in FIG. 12A which illustrates movement of the column 140 in absence of the lateral support tube to explain the tip concept of the present invention. With the lateral support tube (e.g., coil) provided, when the inner catheter is pulled axially with a force P in the proximal direction, the column (e.g., rectangular nitinol wire) will attempt to compress (buckle) axially however it will be restricted by the lateral reinforcement (support), e.g., tube 50. Since the tip can no longer fail axially (in compression), it will fail laterally (deflect) (see FIGS. 13A and 13C). It should be appreciated that axial proximal movement of the inner catheter is discussed. However, it should be appreciated that distal movement of the outer catheter would achieve the same effect. Therefore, as used herein, relative movement includes movement of the inner catheter with respect to the outer catheter, movement of the outer catheter with respect to the inner catheter, or movement of both in opposite directions with respect to each other.

With respect to axial push deflection, when no lateral support tube is present on the distal end of the catheter, the rectangular nitinol wire (or alternate column member structure such as a rod discussed above) is modeled as an eccentrically loaded beam. This means that when the inner shaft is pushed axially with a force P it will apply a moment to the end of the beam (e.g., rectangular nitinol wire), which causes it to bend. This is shown in FIG. 12B, with the lateral support tube (e.g., coil) provided and the inner catheter is pushed axially with a force P in the distal direction, there will be a moment applied to the overall tip causing it to bend (deflect) as shown in FIG. 13B and FIG. 13D. In this case, the addition of the coil does not change the action. It should be appreciated that axial distal movement of the inner catheter is discussed. However, it should be appreciated that proximal movement of the outer catheter would achieve the same effect. Therefore, as used herein, relative movement includes movement of the inner catheter with respect to the outer catheter, movement of the outer catheter with respect to the inner catheter, or movement of both in opposite directions with respect the each other.

Axial pushing and pulling can be considered in terms of an x-y axis. Axial pushing and pulling will happen on the x axis and bending (deflection) will end up at a point (x,y). So for compression of the column, causing the tip to bend to y1 position, the distal end of the tip is traveling in the −x1 direction towards its proximal end (−x2).

Thus, as can be appreciated, in the coaxial catheter arrangement of the present invention, deflection of the distal tip is achieved by an axial motion, rather than a pulling down on the distal tip as in prior art non-coaxial catheters. Thus, the catheter itself is being used to bend the distal tip as opposed to the prior art side by side wire and catheter. Viewed in another way, the bending is achieved not by pulling in the direction of bending but by an axial movement. The structure of the deflectable catheter of the present invention saves space to reduce the overall size (diameter) of the catheter to provide a reduced profile for insertion. It also provides space for fluid flow to enhance deflection (by enhancing relative movement of the inner and outer catheters) without requiring an increase in the size (diameter) of the catheter.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A bi-directional deflectable catheter comprising:
   an outer tubular member having a proximal end, a distal end and a first lumen;
   an inner tubular member having a proximal end and a distal end, the inner member positioned within the first lumen of the outer member, the inner member and outer member being relatively movable, and a distal region of the inner member extending distally of the distal end of the outer member;
   an elongated column member having a proximal end and a distal end, the column member fixed at the distal end of the inner member and fixed at the distal end of the outer member, wherein the column member is configured to bend in a region between the proximal end and the distal end to form an arc having a first height; and
   a restriction member positioned over the column member and distal region of the inner member to restrict the bend of the column member to less than the first height; wherein a distal tip portion of the catheter is deflectable in first and second opposing directions from a longitudinal axis of the catheter.

2. The catheter of claim 1, wherein the column member has a cross-sectional dimension less than a cross-sectional dimension of the distal region of the inner member.

3. The catheter of claim 1 wherein the column member is composed of a different material than the inner member.

4. The catheter of claim 2, wherein the column member is rectangular in cross-section.

5. The catheter of claim 3, wherein the column member is composed of one of stainless steel or nitinol.

6. The catheter of claim 1, wherein the restriction member comprises a compressible coil.

7. The catheter of claim 6, wherein the restriction member is composed of nitinol.

8. The catheter of claim 1, wherein in an absence of the restriction member the column member is bendable into a U-shape.

9. The catheter of claim 1, wherein the column member is deflectable to an angle of 90 degrees with respect to the longitudinal axis.

10. A bi-directional deflectable catheter comprising:
    an outer tubular member having a proximal end, a distal end and a first lumen;
    an inner tubular member having a proximal end, a distal end and a second lumen, the inner member positioned within the first lumen of the outer member, the inner member and outer member being relatively movable, and a distal region of the inner member extending distally of the distal end of the outer member;
    an elongated column member having a proximal end and a distal end, the proximal end of the column member fixed to the distal end of the outer member;
    and the distal end of the column member fixed to the distal end of the inner member, and
    a restriction member positioned over the column member and distal region of the inner member, the restriction member restricting buckling of the column member between the proximal and distal ends and further restricting deflection of a distal tip portion of the catheter, the distal tip portion of the catheter is deflectable in first and second opposing directions from a longitudinal axis of the catheter depending on the direction of relative movement of the inner and outer members.

11. The catheter of claim 10, wherein the column member is composed of a different material than the inner member.

12. The catheter of claim 10, wherein the distal region of the inner member has a lumen having a central longitudinal axis aligned with a central longitudinal axis of the outer member.

13. The catheter of claim 10, wherein the second lumen extends to the distal end of the inner member and the column member is radially offset from the second lumen.

14. The catheter of claim 10, further comprising a marker band at one or both of a region where the column member is fixed to the inner member and a region wherein the column member is fixed to the outer member.

15. The catheter of claim 10, wherein the distal region of the inner member is tubular.

16. A deflectable microcatheter comprising:
- an outer catheter having a proximal end, a distal end and a first lumen;
- an inner catheter having a proximal end, a distal end and a deflectable tip, a distal region of the inner member extending distally of the distal end of the outer catheter;
- a restriction member positioned over the deflectable tip; and
- a column member positioned within the restriction member and attached at the distal end of the outer catheter and at the distal end of the inner catheter;
- wherein proximal movement of the inner catheter applies a proximal force to the column member, thereby bending the deflectable tip of the inner catheter in a direction away from the column member; and
- wherein distal movement of the inner catheter applies a distal force to the column member, thereby bending the deflectable tip of the inner catheter in a direction toward the column member.

17. The microcatheter of claim 16, wherein the column member has a cross-sectional dimension less than a cross sectional dimension of the distal region of the inner catheter extending distally of the outer catheter.

18. The microcatheter of claim 17, wherein the outer catheter has a central longitudinal axis and the column member is radially offset with respect to the central longitudinal axis of the outer catheter.

19. The microcatheter of claim 17, wherein distal movement of the outer catheter applies a distal force to the column member, thereby bending the deflectable tip of the inner catheter in a direction away from the column member and proximal movement of the outer catheter applies a proximal force to the column member, thereby bending the deflectable tip of the inner catheter in a direction toward the column member.

* * * * *